(12) United States Patent
Breu et al.

(10) Patent No.: US 9,342,651 B2
(45) Date of Patent: May 17, 2016

(54) COMPUTATIONAL METHODS FOR TRANSLATING A SEQUENCE OF MULTI-BASE COLOR CALLS TO A SEQUENCE OF BASES

(75) Inventors: Heinz Breu, Palo Alto, CA (US); Danwei Guo, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1041 days.

(21) Appl. No.: 13/106,998

(22) Filed: May 13, 2011

(65) Prior Publication Data

US 2011/0295514 A1     Dec. 1, 2011

Related U.S. Application Data

(60) Provisional application No. 61/334,537, filed on May 13, 2010.

(51) Int. Cl.
*G06F 19/22* (2011.01)
*G06F 15/00* (2006.01)
*C12Q 1/68* (2006.01)

(52) U.S. Cl.
CPC .............. *G06F 19/22* (2013.01); *C12Q 1/6869* (2013.01)

(58) Field of Classification Search
CPC ......... G06F 19/22; G06F 19/18; G06F 19/10; G06F 19/12; C12Q 1/6809; C12Q 1/6869; C12Q 1/6883; C12Q 2525/117; C12Q 1/04; C12Q 1/68; C12Q 1/6806; C12Q 1/6874; C12Q 1/6886; C12Q 1/6888; C12Q 1/689; C12Q 2523/125; C12Q 2537/16; C12Q 2537/165

See application file for complete search history.

(56) References Cited

U.S. PATENT DOCUMENTS

2009/0062129 A1    3/2009   McKernan et al.

FOREIGN PATENT DOCUMENTS

WO    WO-2006/084132    8/2006

OTHER PUBLICATIONS

Shendure et al. Next-generation DNA sequencing Nature Biotechnology vol. 26, pp. 1135-1145 (2008).*
Breu, H., "A theoretical understanding of 2 base color codes and its application to annotation, error detection, and error correction", (http://www3.appliedbiosystems.com/cms/groups/mcb_marketing/documents/generaldocuments/cms_858265.pdf), Jul. 2010.
Li, H. et al., "Mapping short DNA sequencing reads and calling variants using mapping quality scores", *Genome Research*, vol. 18, Aug. 19, 2008, 1851-1858.
Ondov, B. D. et al., "Efficient mapping of applied biosystems SOLiD sequence data to a reference genome for functional genomic applications", *Bioinformatics*, vol. 24, No. 23, Oct. 7, 2008, 2776-2777.
PCT/US2011/036393, International Search Report and Written Opinion mailed on Feb. 9, 2012.
Rumble, S. M. et al., "SHRiMP: Accurate mapping of short colorspace 1-30 reads", *PLOs Computational Biology*, vol. 5, issue 5, May 22, 2009, e1000385.
Salmela, L., "Correction of sequencing errors in a mixed set of reads", *Bioinformatics*, vol. 26, No. 10, Apr. 8, 2010, 1284-1290.
U.S. Appl. No. 12/873,132, "Fast-Indexing Filter Wheel and Method of Use," specification and figures, 56 pages, filed Aug. 31, 2010.
U.S. Appl. No. 12/873,190, "Low-Volume Sequencing System and Method of Use," specification and figures, 56 pages, filed Aug. 31, 2010.
Applied Biosystems, "Principles of Di-Base Sequencing and the Advantages of Color Space Analysis in the SOLiD™ System," 4 pages, Apr. 2008.
Applied Biosystems, "A Theoretical Understanding of 2 Base Color Codes and Its Application to Annotation, Error Detection, and Error Correction," 12 pages, Jun. 2008.

* cited by examiner

*Primary Examiner* — John S Brusca

(57) ABSTRACT

Disclosed are systems and methods for resequencing using color calls. A DNA sample is encoded and sequenced according to a multi-base code producing a string of read color calls for a fragment of the sample. A reference sequence is obtained. The string of read color calls is mapped to the reference sequence. A base sequence is extracted from the reference sequence. The base sequence is encoded as a string of reference color codes according to the multi-base code. The string of read color calls is aligned with the string of reference color codes and mismatches in the alignment are detected. One or more mismatches of the string of read color calls are annotated as inconsistent. The one or more inconsistent mismatches of the string of read color calls are corrected. The string of corrected read color calls is decoded to bases producing a read sequence.

18 Claims, 14 Drawing Sheets

SEQUENCE LISTING

<160> NUMBER OF SEQ ID NOS: 7

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atcaagcctc                                                              10

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcggaatatc cgtccaa                                                      17

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gaatatccgt c                                                            11

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 4
gcgsaawwtc nvthcaa                                                      17

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other
<220> FEATURE:

```
<221> NAME/KEY: modified_base
<222> LOCATION: (11)..(11)
<223> OTHER INFORMATION: a, c, t, g, unknown or other

<400> SEQUENCE: 5
naanntcnnt n                                                           11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caaaatcaat a                                                           11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaaaatccct t                                                           11
```

COMPUTATIONAL METHODS FOR TRANSLATING A SEQUENCE OF MULTI-BASE COLOR CALLS TO A SEQUENCE OF BASES

SEQUENCE LISTING

The instant application contains a Sequence Listing which has been submitted in ASCII format via EFS-Web and is hereby incorporated by reference in its entirety. Said ASCII copy, created on Aug. 9, 2011, is named LT00205.txt and is 2,393 bytes in size.

FIELD

The present disclosure generally relates to the field of DNA sequencing technology, and more particularly to systems and methods for reconstructing a sequence of bases for a fragment from its sequence of color calls and a reference sequence.

INTRODUCTION

Once a reference sequence is available for a genome, comparative sequencing or resequencing can be used to characterize the genetic diversity among individual genomes of the same type or within the same species or between genomes of different species. The ability to generate sufficient depth of coverage for variant detection across an entire genome or between genomes of different species can be limited by the throughput of the nucleic acid sequencing system, technology, or instrument.

Next generation sequencing (NGS) technologies offer a solution to this problem by providing high throughput DNA sequencing. Certain NGS technologies, such as the SOLiD™ System from Life Technologies, employ a scheme that represents fragments of DNA as a sequence of overlapping dibases (adjacent pairs of bases). The system encodes each dibase with one of four colors using a coding scheme that results in a sequence of color calls that represent a nucleotide sequence. As a result, resequencing using a dibase encoding system, such as the SOLiD™ System, involves generating fragments represented by a sequence of color calls.

SUMMARY

In various embodiments, a method for resequencing using color calls can include obtaining a string of read color calls encoded according to a multi-base code. The method can include encoding a reference sequence as a string of reference color codes according to the multi-base code. The method can include aligning the string of read color calls with the string of reference color codes and detecting mismatches in the alignment. The method can include annotating one or more mismatches of the string of read color calls as inconsistent, and correcting the one or more mismatches of the string of read color calls. These and other features are provided herein.

BRIEF DESCRIPTION OF THE DRAWINGS

The skilled artisan will understand that the drawings, described below, are for illustration purposes only. The drawings are not intended to limit the scope of the present teachings in any way.

FIG. 5 is an exemplary base sequence extraction showing how a base sequence (SEQ ID NO: 5) is extracted from a reference sequence (SEQ ID NO: 4) using a missing code when the reference sequence includes ambiguity codes, in accordance with certain embodiments.

FIG. 6 is an exemplary base sequence extraction showing how a base sequence (SEQ ID NO: 6) is extracted from a reference sequence (SEQ ID NO: 4) using alphabetically a first base from an ambiguity code when the reference sequence includes ambiguity codes, in accordance with certain embodiments.

Figure 1:
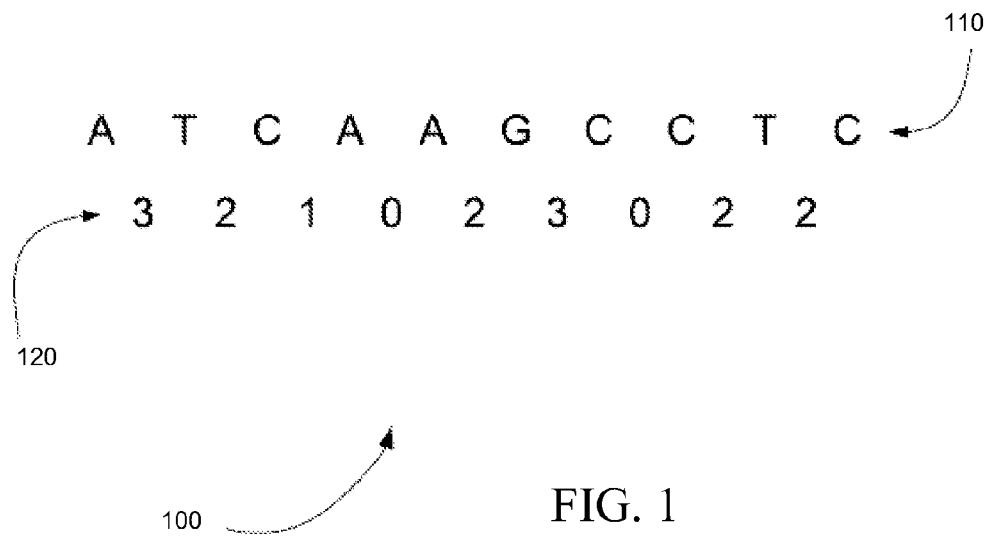
FIG. 1 shows an encoding of the DNA sequence ATCAAGCCTC (SEQ ID NO: 1) using an exemplary dibase coding scheme, in accordance with certain embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts.

DESCRIPTION OF VARIOUS EMBODIMENTS

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As utilized in accordance with the embodiments provided herein, the following terms, unless otherwise indicated, shall be understood to have the following meanings:

As used herein, "a" or "an" means "at least one" or "one or more". Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

The phrase "next generation sequencing" refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the SOLiD Sequencing System of Life Technologies Corp. provides massively parallel sequencing with enhanced accuracy. The SOLiD System and associated workflows, protocols, chemistries, etc. are described in more detail in PCT Publication No. WO 2006/084132, entitled "Reagents, Methods, and Libraries for Bead-Based Sequencing," international filing date Feb. 1, 2006, U.S. patent application Ser. No. 12/873,190, entitled "Low-Volume Sequencing System and Method of Use," filed on Aug. 31, 2010, and U.S. patent application Ser. No. 12/873,132, entitled "Fast-Indexing Filter Wheel and Method of Use," filed on Aug. 31, 2010, the entirety of each of these applications being incorporated herein by reference thereto.

The phrase "sequencing run" refers to any step or portion of a sequencing experiment performed to determine some information relating to at least one biomolecule (e.g., nucleic acid molecule).

The phrase "ligation cycle" refers to a step in a sequence-by-ligation process where a probe sequence is ligated to a primer or another probe sequence.

The phrase "color call" refers to an observed dye color that results from the detection of a probe sequence after a ligation cycle of a sequencing run. Similarly, other "calls" refer to the distinguishable feature observed.

The phrase "fragment library" refers to a collection of nucleic acid fragments, wherein one or more fragments are used as a sequencing template. A fragment library can be generated, for example, by cutting or shearing a larger nucleic acid into smaller fragments. Fragment libraries can be generated from naturally occurring nucleic acids, such as bacterial nucleic acids. Libraries comprising similarly sized synthetic nucleic acid sequences can also be generated to create a synthetic fragment library.

The phrase "paired-end library" refers to a collection of nucleic acid fragments, wherein one or more fragments are used as a sequencing template to obtain sequence information from both ends of the fragment. A paired-end library can be generated, for example, by cutting or shearing a larger nucleic acid into smaller fragments. Paired-end libraries can be generated from naturally occurring nucleic acids, such as bacterial nucleic acids. Libraries comprising similarly sized synthetic nucleic acid sequences can also be generated to create a synthetic fragment library.

The phrase "mate-pair library" refers to a collection of nucleic acid sequences comprising two fragments having a relationship, such as by being separated by a known number of nucleotides. Mate pair fragments can be generated by cutting or shearing, or they can be generated by circularizing fragments of nucleic acids with an internal adapter construct and then removing the middle portion of the nucleic acid fragment to create a linear strand of nucleic acid comprising the internal adapter with the sequences from the ends of the nucleic acid fragment attached to either end of the internal adapter. Like fragment libraries, mate-pair libraries can be generated from naturally occurring nucleic acid sequences. Synthetic mate-pair libraries can also be generated by attaching synthetic nucleic acid sequences to either end of an internal adapter sequence.

The term "template" and variations thereof refer to a nucleic acid sequence that is a target of nucleic acid sequencing. A template sequence can be attached to a solid support, such as a bead, a microparticle, a flow cell, or other surface or object. A template sequence can comprise a synthetic nucleic acid sequence. A template sequence also can include an unknown nucleic acid sequence from a sample of interest and/or a known nucleic acid sequence.

The present disclosure generally relates to the field of nucleic acid sequencing technology, and more particularly, to systems and methods for reconstructing a sequence of bases for a fragment based on its sequence of color calls and a reference sequence. In certain nucleic acid sequencing systems, a sequence of a nucleic acid strand can be determined by identifying nucleotides that form base pairs with respective nucleotides of the strand. Such base-pairing reactions can be achieved so as to identify one nucleotide at a time, or two or more nucleotides can be identified by interrogating such nucleotides with appropriately configured probes.

The SOLiD™ System, marketed by Life Technologies, is an example of nucleic acid sequencing system where more than one nucleotide is interrogated at a time. This system utilizes probes that interrogate two (or more) nucleotides at a time. By also utilizing initializing probes that allow different, off-sets starting locations relative the fragment sequence to be interrogated for multiple cycles of ligation reactions, each nucleotide of a template strand being analyzed can be probed two or more times so as to yield a robust base-calling accuracy and reliability. Additional details concerning the SOLiD™ System can be found, for example, in U.S. patent application Ser. No. 11/737,308 filed Apr. 19, 2007 and entitled "REAGENTS, METHODS, AND LIBRARIES FOR GEL-FREE BEAD-BASED SEQUENCING" (Publication No. 2009/0062129) which is incorporated herein by reference in its entirety.

In various embodiments, methods provided herein can include obtaining a string of color calls during or from a sequencing process or experiment (herein referred to as "read color calls"). The read color calls can be encoded according to a dibase or other multi-base code. A known or reference base sequence can be encoded as a string of dibase or other multi-base color calls according to the dibase or multi-base code (herein referred to as "reference color calls"). Methods provided by this disclosure can include aligning or mapping the string of read color calls with the string of reference color calls and detecting mismatches in the alignment. One or more mismatches of the string of read color calls can be annotated as inconsistent, and one or more mismatches of the string of read color calls can be corrected. These and other features are provided herein.

Table 1 shows an exemplary dibase coding scheme, in accordance with certain embodiments. The column under code i lists the corresponding dye and the dibases (adjacent nucleotides) encoded by color i. For example, GT is labeled with Cy3 and coded as "1". A DNA sequence, such as ATCAAGCCTC (SEQ ID NO: 1), is encoded, for example, by starting at the 5' end, replacing the dimer AT at this position with its corresponding code 3 from Table 1, advancing by one base, which exposes the TC dimer, and continuing.

TABLE 1

| CODE | 0 | 1 | 2 | 3 |
|---|---|---|---|---|
| DYE | FAM | CY3 | TXR | CY5 |
| (XY)1 | AA | AC | AG | AT |
| (XY)2 | CC | CA | GA | TA |
| (XY)3 | GG | GT | CT | CG |
| (XY)4 | TT | TG | TC | GC |

FIG. 1 shows an encoding 100 of the DNA sequence ATCAAGCCTC (SEQ ID NO: 1) using an exemplary dibase coding scheme, in accordance with certain embodiments. Base sequence 110 is encoded as color string 120 in encoding 100 using the exemplary dibase coding scheme shown in Table 1. This process encodes a k-mer of bases as a (k-1)-mer of colors. This color string is ambiguous in the sense that it codes for four different k-mers, but that the color string can be disambiguated with knowledge of the type and position of any of its k bases. Therefore, it is traditional to prepend the leading base, when known, resulting in a k-mer of the form A321023022 for encoding 100 shown in FIG. 1, from which the base sequence can be reconstructed.

The exemplary dibase coding scheme shown in Table 1 possesses certain properties. These properties can be treated as requirements and used to reconstruct the color code. A first property can be that each dibase is represented by one of four available colors. These colors can be denoted as 0, 1, 2, and 3, for example. A second property can be that two dibases that nevertheless have the same first base get different colors. For example, the color of AC may not be equal to the color of AG. A third property can be that a dibase and its reverse get the same color. For example, the color of AC can be equal to the color of CA. A fourth property can be that monodibases get the same color. So, AA, CC, GG, and TT can all have the same color.

Other properties can follow from the four properties just outlined. A fifth property can follow from the second property and the third property. The fifth property can be that two different dibases that nevertheless have the same second base get different colors. For example, the color of AC may not be equal to the color of TC. A sixth property can follow from the first property and the fourth property. The sixth property can be that a dibase and its complement get the same color. For example, the color of AC can be equal to the color of TG.

Tables 2-5 show the construction of an exemplary dibase coding scheme by treating the properties described above as requirements. The dibase coding scheme shown in Tables 2-5 is the same as the dibase coding scheme shown in Table 1. The notations used in Tables 2-5 and Table 1 are different, however. In Tables 2-5 the rows and columns represent the first bases and second bases of each dibase, respectively. The cells of each table show the color code for each dibase. In Table 1, in contrast, the columns represent the color code and each cell of the table includes a dibase.

Table 2 shows construction of an exemplary dibase coding scheme using the requirements that there are four different colors and two dibases that have the same first base get different colors, in accordance with certain embodiments. These two requirements can spring from the first and second properties described above. From these two requirements, all four colors can be present in the first row. Any one-to-one mapping between the actual dyes and the color code labels 0, 1, 2, and 3 can be used. In Table 2, the labels are shown in row A in consecutive order, for example.

TABLE 2

|  |  | Second Base | | | |
|---|---|---|---|---|---|
|  |  | A | C | G | T |
| First Base | A | 0 | 1 | 2 | 3 |
|  | C |  |  |  |  |
|  | G |  |  |  |  |
|  | T |  |  |  |  |

Table 3 shows the further construction of an exemplary dibase coding scheme using the requirement that a dibase and its reverse get the same color, in accordance with certain embodiments. This requirement can spring from the third property described above. If row A has labels 0, 1, 2, and 3 in consecutive order, then column A can also have labels 0, 1, 2, and 3 in consecutive order, for example.

TABLE 3

|  |  | Second Base | | | |
|---|---|---|---|---|---|
|  |  | A | C | G | T |
| First Base | A | 0 | 1 | 2 | 3 |
|  | C | 1 |  |  |  |
|  | G | 2 |  |  |  |
|  | T | 3 |  |  |  |

Table 4 shows the further construction of an exemplary dibase coding scheme using the requirement that monodibases get the same color, in accordance with certain embodiments. This requirement can spring from the fourth property described above. If cell AA has label 0, then cells CC, GG, and TT can also have label 0, for example.

TABLE 4

|  |  | Second Base | | | |
|---|---|---|---|---|---|
|  |  | A | C | G | T |
| First Base | A | 0 | 1 | 2 | 3 |
|  | C | 1 | 0 |  |  |
|  | G | 2 |  | 0 |  |
|  | T | 3 |  |  | 0 |

Table 5 shows the final construction of an exemplary dibase coding scheme using the requirements that there are four different colors, two dibases that have the same first base get different colors, and two different dibases that have the same second base get different colors, in accordance with certain embodiments. These three requirements can spring from the first, second, and fifth properties described above. From these three requirements, the empty six cells shown in Table 4 can be filled as shown in Table 5, for example.

TABLE 5

|  |  | Second Base | | | |
|---|---|---|---|---|---|
|  |  | A | C | G | T |
| First Base | A | 0 | 1 | 2 | 3 |
|  | C | 1 | 0 | 3 | 2 |
|  | G | 2 | 3 | 0 | 1 |
|  | T | 3 | 2 | 1 | 0 |

In various embodiments, the dibase coding scheme shown in Table 5 can be used to determine a sequence of bases of a nucleic acid fragment. A nucleic acid sequencer can interrogate the nucleic acid fragment to produce a string of read color calls. The string of read color calls can be mapped to a reference sequence, such as a reference sequence obtained from a database. A base sequence can be extracted from the reference sequence, and the base sequence can be encoded as a string of reference color codes according to the dibase code. The string of read color calls can be aligned with the string of reference color codes and mismatches can be detected in the alignment. The mismatches can be annotated as consistent or inconsistent. The string of read color calls can be corrected, and the corrected string of read color calls can be decoded to the bases producing the read sequence.

Figure 2:
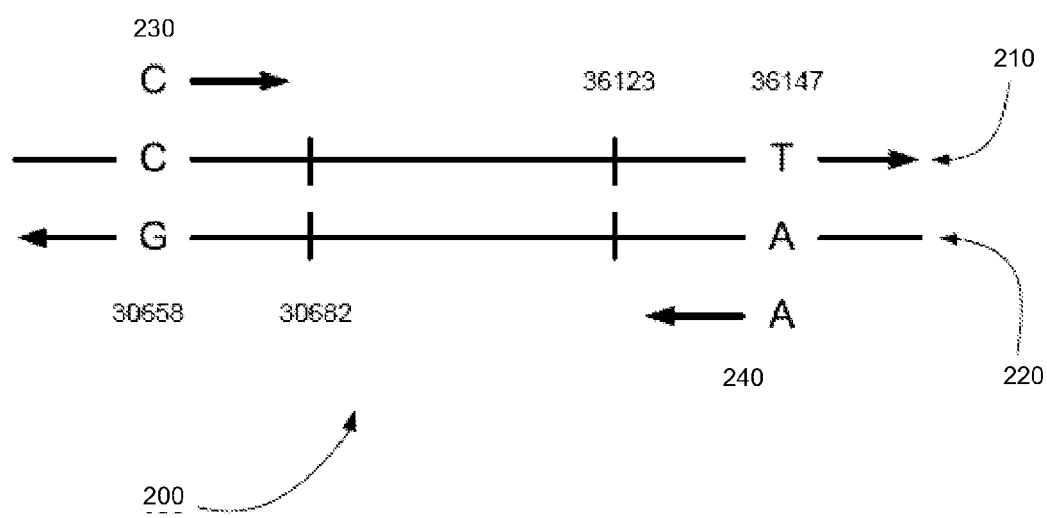
FIG. 2 is an exemplary alignment showing a string of color calls mapped to a reference sequence, in accordance with certain embodiments.

FIG. 2 is an exemplary alignment 200 showing two strings of color calls mapped to a reference sequence, in accordance with certain embodiments. In alignment 200, the string of color calls 230 beginning with base C can be mapped to reference forward strand 210 between positions 30,658 and 30,682. The string of color calls 240 beginning with base A can be mapped to reference reverse strand 220 of the same reference, between positions 36,123 and 36,147. In particular embodiments, the string of color calls 230 and the reference forward strand 210 between positions 30,658 and 30,682 can have a substantially similar sequence of color codes. For example, the string of color calls 230 and the reference forward strand 210 between positions 30,658 and 30,682 can have greater than 50% similarity, such as greater than 75% similarity, such as greater than 80% similarity, such as greater than 90% similarity, even greater than 95% similarity. Similarly, the string of color calls 240 and the reference reverse strand 220 between positions 36,123 and 36,147 can have a substantially similar sequence of color codes. Various algorithms for mapping a string to a reference string are known in the art.

Base Sequence Extraction

Figure 3:
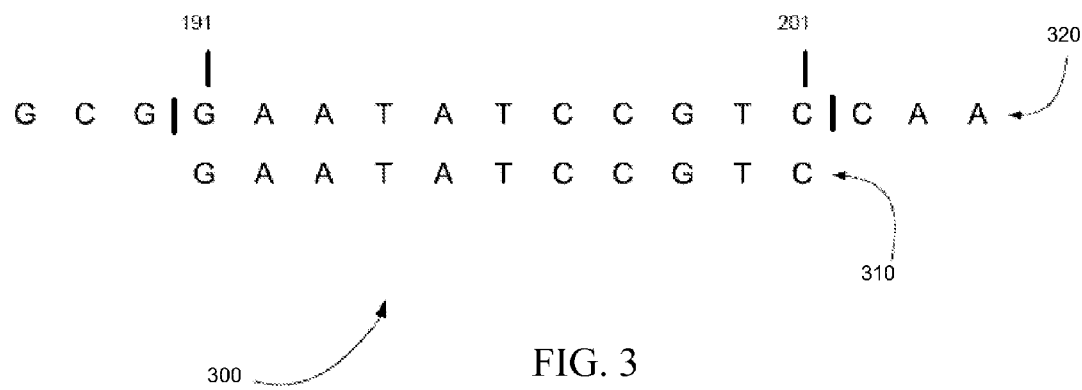
FIG. 3 is an exemplary base sequence extraction showing how a base sequence (SEQ ID NO: 3) is extracted from a reference sequence (SEQ ID NO: 2) when the reference sequence does not include any ambiguity codes, in accordance with certain embodiments.

FIG. 3 is an exemplary base sequence extraction 300 showing how a base sequence can be extracted from a reference sequence when the reference sequence does not include any ambiguity codes, in accordance with certain embodiments. In base sequence extraction 300, base sequence 310 can be extracted from reference sequence 320 for a string of color calls mapped to positions 191 through 201. The position values can be needed to define the range, but the string of color calls itself may not be needed. The reference characters in this range can be all bases A, C, G, or T. As a result, the subsequence defined by the map can be returned as base sequence 310. Base sequence extraction can be more difficult when the reference contains ambiguity codes.

Table 6 shows the International Union of Biochemistry (IUB) codes that include definitions of ambiguity codes, in accordance with certain embodiments.

TABLE 6

| Code | Definition |
|---|---|
| A | {A} |
| C | {C} |
| G | {G} |
| T | {T} |
| R | {A, G} |
| Y | {C, T} |
| K | {G, T} |
| M | {A, C} |
| S | {C, G} |
| W | {A, T} |

TABLE 6-continued

| Code | Definition |
| --- | --- |
| B | {C, G, T} |
| D | {A, G, T} |
| H | {A, C, T} |
| V | {A, C, G} |
| N | {A, C, G, T} |

Figure 4:
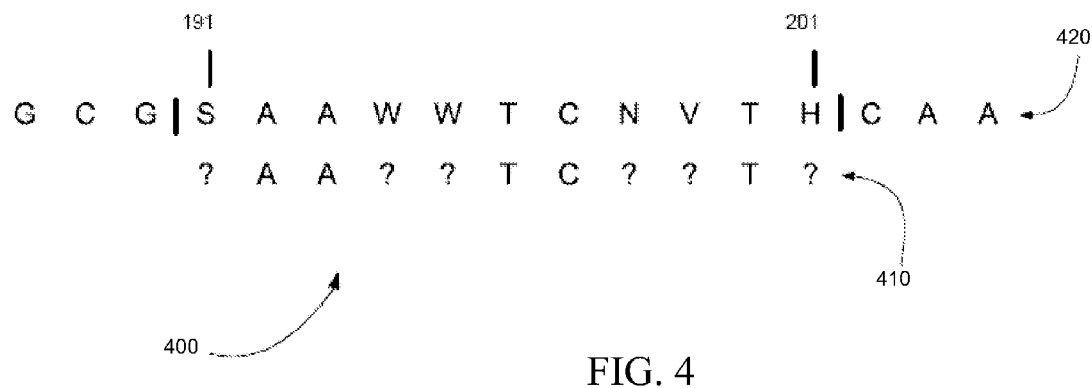
FIG. 4 is an exemplary base sequence extraction showing the problem of extracting a base sequence (SEQ ID NO: 5) from a reference sequence (SEQ ID NO: 4) when the reference sequence does include ambiguity codes, in accordance with certain embodiments.

FIG. 4 is an exemplary base sequence extraction 400 showing the problem of extracting a base sequence from a reference sequence when the reference sequence does include ambiguity codes, in accordance with certain embodiments. In base sequence extraction 400, base sequence 410 can be extracted from reference sequence 420 for a string of color calls mapped to positions 191 through 201. Reference sequence 420 can include ambiguity codes S, W, N, V, and H. For example, the reference sequence 420 can include ambiguity codes where the sequence data is poorly determined, where there are allelic variations in an individual or set of individuals from which the reference sequence was derived, or the like. These ambiguity codes are defined in Table 6, for example. Because ambiguity codes can represent two, three, or four possible bases, base sequence 410 of FIG. 4 may not be well defined in the range 191 through 201.

Embodiment Relating to Ambiguity to Missing Extraction

FIG. 5 is an exemplary base sequence extraction 500 showing how a base sequence can be extracted from a reference sequence using a missing code when the reference sequence includes ambiguity codes, in accordance with certain embodiments. In base sequence extraction 500, base sequence 510 can be extracted from reference sequence 520 between positions 191 and 201 and any ambiguity codes can be converted to the missing base code 'x'. Note that the 'x's are shown in lower case only to indicate that they differ from the reference.

In various embodiments, the method shown in base sequence extraction 500 of FIG. 5 can be used extract a base sequence from a reference sequence when the reference sequence includes at least one ambiguity code. If the reference sequence to which the string of read color calls maps or aligns includes an ambiguity code, the base sequence can be extracted from the reference sequence by replacing the ambiguity code with a missing base code. Further, the extracted base sequence that includes the missing base code can be encoded as a string of reference color codes by utilizing a missing color code for the missing base code and one or more adjacent base codes. The missing color code can be '.', for example. The conversion of base codes to color codes is then color(Ax)=color(xx)=color(xT)='.', for example.

Embodiment Relating to Ambiguity to First

FIG. 6 is an exemplary base sequence extraction 600 showing how a base sequence can be extracted from a reference sequence using alphabetically a first base from an ambiguity code when the reference sequence includes ambiguity codes, in accordance with certain embodiments. In base sequence extraction 600, base sequence 610 can be extracted from reference sequence 620 between positions 191 and 201 and each ambiguity code can be converted to the first base alphabetically in the list of bases for that ambiguity code. Note that the converted codes are shown in lower case only to indicate that they differ from the reference. This method can be biased toward alphabetically low bases. The bias can be eliminated by selecting a base not alphabetically, but at random. Although such a method would not be deterministic in theory, it could be in practice, because it could use a pseudo-random number generator, and that generator could be "seeded".

In various embodiments, the method shown in base sequence extraction 600 of FIG. 6 can be used to extract a base sequence from a reference sequence when the reference sequence includes at least one ambiguity code. If the mapping of the string of read color calls to the reference sequence includes an ambiguity code, the base sequence can be extracted from the reference sequence by replacing the ambiguity code with the first base of an alphabetical listing of bases for that ambiguity code.

Embodiment Relating to Ambiguity to Haplotype

Ambiguity codes in a reference sequence can result in two or more base sequence haplotypes. The term haplotype is used here as shorthand for a sequence of bases, each of which belongs to its corresponding IUB coded set. For example, referring to Table 6, the sequence ACCT is a haplotype of RCYN. The term haplotype is not being used in the biological sense of a sequence of DNA inherited as a unit, although any of the haplotypes discussed here may be inherited as a unit.

In certain embodiments, an optimal base sequence haplotype can be selected from two or more base sequence haplotypes that are extracted from a reference sequence that includes ambiguity codes. The optimal base sequence haplotype can be optimal in that its multi-base-color encoded string minimizes the number of mismatches with the string of read colors calls for a fragment.

Figure 7:
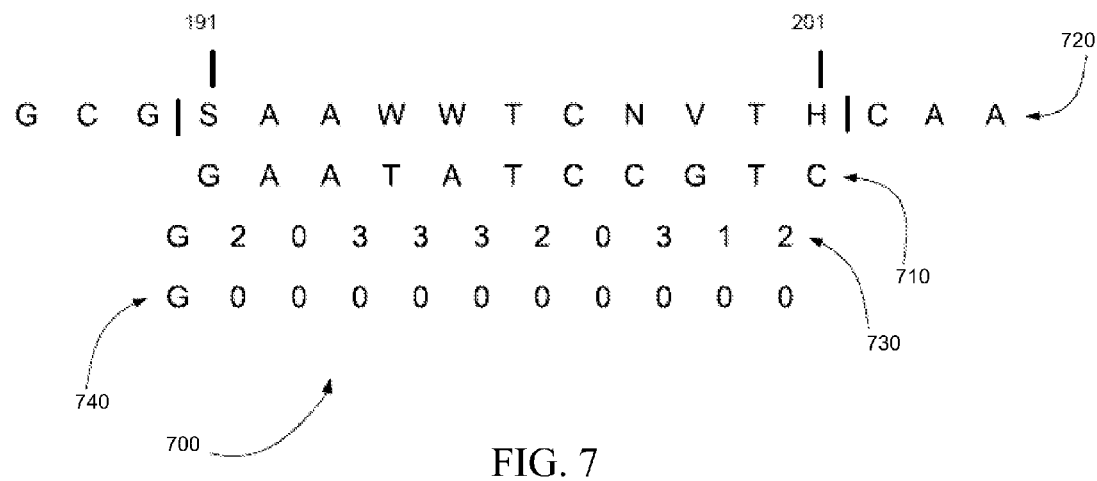
FIG. 7 is an exemplary base sequence extraction showing a base sequence (SEQ ID NO: 3) extracted from a reference sequence (SEQ ID NO: 4) that encodes to a dibase color string that has eight mismatches with a string of read colors calls for a fragment, in accordance with certain embodiments.

FIG. 7 is an exemplary base sequence extraction 700 showing a base sequence extracted from a reference sequence that can encode to a dibase color string that has eight mismatches with a string of read colors calls for a fragment, in accordance with certain embodiments. In base sequence extraction 700, base sequence 710 can be extracted from reference sequence 720 between positions 191 and 201 and each ambiguity code can be converted to a base from the list of bases for that ambiguity code. Base sequence 710 can encode to dibase color string 730 according to the dibase code shown in Table 5, for example. A fragment can be sequenced as string of read colors calls 740, so dibase color string 730 has eight mismatches with string of read colors calls 740.

Figure 8:
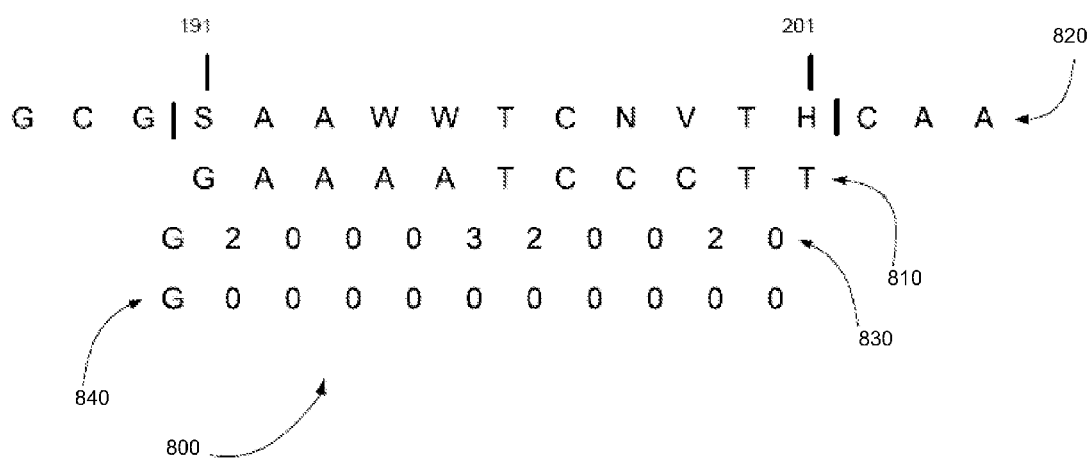
FIG. 8 is an exemplary base sequence extraction showing a base sequence (SEQ ID NO: 7) extracted from a reference sequence (SEQ ID NO: 4) that encodes to a dibase color string that has four mismatches with a string of read colors calls for a fragment, in accordance with certain embodiments.

FIG. 8 is an exemplary base sequence extraction 800 showing a base sequence extracted from a reference sequence that can encode to a dibase color string that has four mismatches with a string of read colors calls for a fragment, in accordance with certain embodiments. In base sequence extraction 800, base sequence 810 can be extracted from reference sequence 720 between positions 191 and 201 and each ambiguity code can be converted to a base from the list of bases for that ambiguity code. Base sequence 810 can encode to dibase color string 830 according to the dibase code shown in Table 5, for example. A fragment can be sequenced as string of read colors calls 740, so dibase color string 830 has four mismatches with string of read colors calls 740.

Base sequence 710 of FIG. 7 and base sequence 810 of FIG. 8 can be both base sequence haplotypes of reference sequence 720. Base sequence 810 of FIG. 8, however, can provide a more optimal base sequence haplotype because its dibase color string 830 has fewer mismatches with string of read colors calls 740.

In various embodiments, a method of selecting an optimal base sequence haplotype can be used when the reference sequence includes one or more ambiguity codes. If the mapping of the string of read color calls to the reference sequence includes one or more ambiguity codes, multiple base sequences can be extracted from the reference sequence. Each of the base sequences can be encoded as a string of reference color codes, and the optimal string of reference color codes can be selected. Two or more base sequences can be from the reference sequence by replacing the one or more ambiguity codes with different possible bases. Each of the two or more base sequences can be encoded according to the dibase code shown in TABLE 5, for example, producing two or more strings of base color calls. Each of the two or more strings of base color calls can be compared to the string of read color calls. The string of reference color codes that has the minimum number of mismatches with the string of read color calls can be selected as the string of reference color codes of the base sequence that is used in resequencing.

Align Read and Base Color Calls

Figure 9:
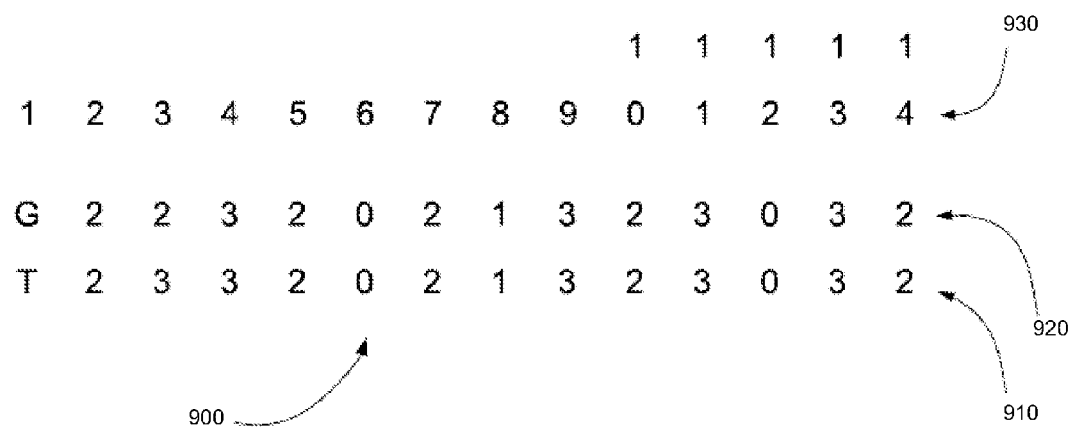
FIG. 9 is an exemplary alignment of a string of read color calls with a string of reference color calls, in accordance with certain embodiments.

FIG. 9 is an exemplary alignment 900 of a string of read color calls with a string of reference color codes, in accordance with certain embodiments. In alignment 900, string of read color calls 910 can be aligned with string of reference color codes 920 according to position 930. Note that string of read color calls 910 can differ with string of reference color codes 920 in positions 1 and 3. These mismatches can be annotated.

Mismatch Annotation

In any given resequencing experiment, base variants can occur in isolated adjacent clusters. A single nucleotide polymorphism (SNP), for example, is one kind of one-base variant, but a double nucleotide polymorphism (DNP), which is a two-base variant, or even a three-base mutation, which would be a three-base variant are also possible.

A color call from a read can be consistent with a conserved base, it can be consistent with a variant of one, two, or three adjacent bases, or it can be inconsistent with any of these. Annotations can be made in the form of a "tint" code to suggest that annotated color reads should be rendered in different tints by a browser, for example. The nature and number of these tints can also be user selectable.

Five tint codes can be used, for example. These tint codes are 'a' for gray, 'g' for green, 'y' for yellow, 'r' for red, and 'b' for blue. Gray or 'a' can signify a color mismatch position that is inconsistent with a zero-, one-, two-, or three-base variant, and is not adjacent to another mismatch. Green or 'g' can signify that a color position is consistent with an isolated one-base variant (e.g. a SNP). Yellow or 'y' can signify that a color position is consistent with an isolated two-base variant. Red or 'r' can signify that a color position is consistent with an isolated three-base variant. Finally, blue or 'b' can signify a color mismatch position that is inconsistent with a zero-, one-, two-, or three base variant, but is adjacent to another mismatch. Therefore tint codes 'a' and 'b' can signify that a color call is inconsistent, and tint codes 'g', 'y', and 'r' signify that a color call is consistent.

Read Color Call Correction

Read color calls annotated with a consistent tint code can be likely to represent a true base variant. As a result, these read color calls may not be corrected. Read color calls annotated with an inconsistent tint code, however, can be likely to represent sequencing error. As a result, these read color calls can be corrected. A number of methods are available to correct read color calls that are annotated as inconsistent.

Embodiment for Correct to Reference

Figure 10:
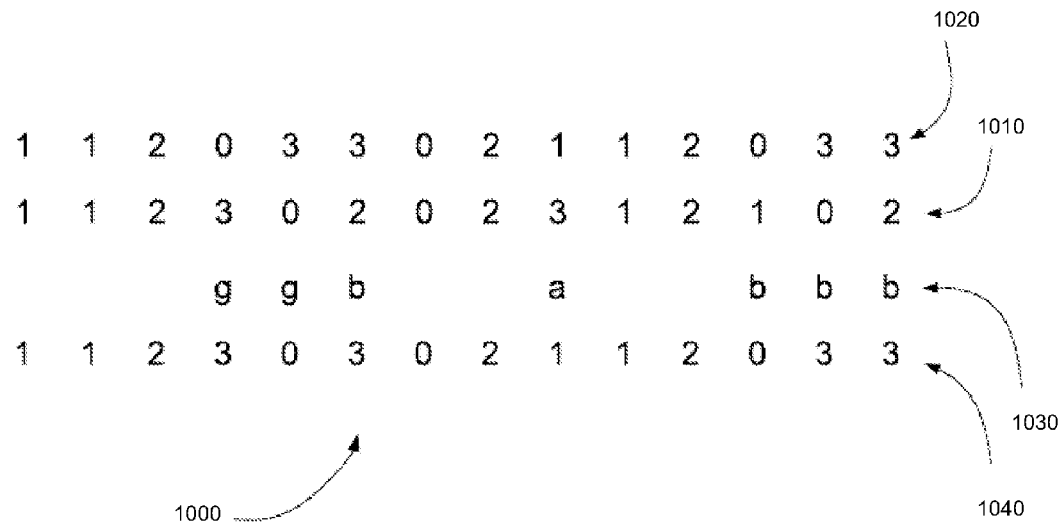
FIG. 10 is an exemplary read color call correction in which read color calls annotated as inconsistent are corrected to the corresponding reference color call, in accordance with certain embodiments.

FIG. 10 is an exemplary read color call correction 1000 in which read color calls annotated as inconsistent are corrected to the corresponding base color call, in accordance with certain embodiments. In read color call correction 1000, string of read color calls 1010 can be aligned with string of reference color codes 1020. String of read color calls 1010 can be annotated with tint codes 1030. Each base of string of read color calls 1010 annotated with an inconsistent-tint code ('a' or 'b') can be replaced in corrected string of read color calls 1040 with the corresponding color call of string of reference color codes 1020. Each color call of string of read color calls 1010 annotated with a consistent tint code or not annotated at all can be copied to corrected string of read color calls 1040.

In various embodiments, the method shown in read color call correction 1000 in FIG. 10 can be used to correct a string of read color calls. One or more mismatches of the string of read color calls can be annotated as inconsistent. The one or more inconsistent mismatches of the string of read color calls can be corrected by replacing each of the one or more inconsistent mismatches with its corresponding color call from the string of reference color codes.

Embodiment for Correct to Missing

Figure 11:
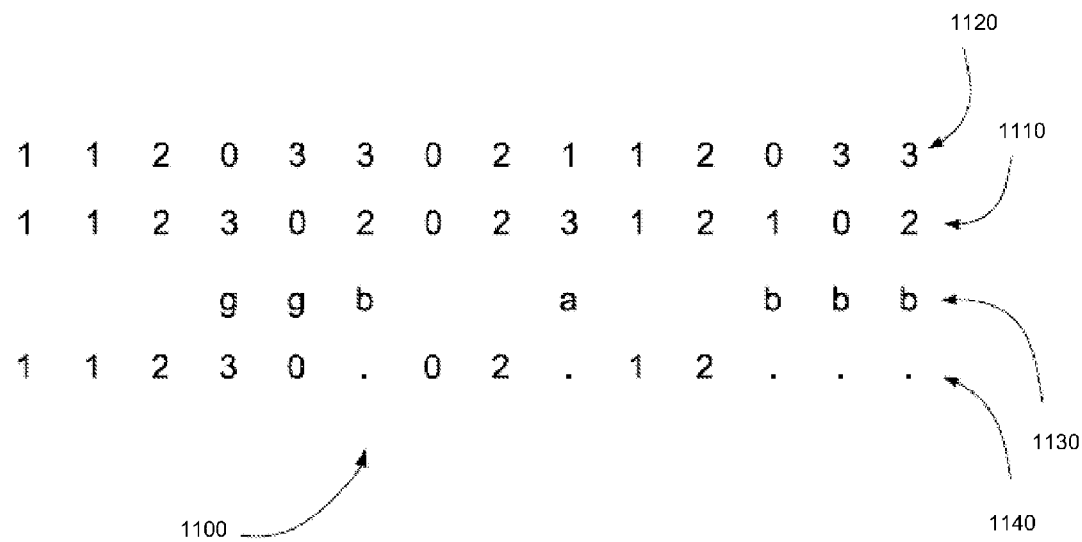
FIG. 11 is an exemplary read color call correction in which read color calls annotated as inconsistent are corrected to the missing color call, in accordance with certain embodiments.

FIG. 11 is an exemplary read color call correction 1100 in which read color calls annotated as inconsistent are corrected to the missing color call, in accordance with certain embodiments. In read color call correction 1100, string of read color calls 1110 can be aligned with string of reference color codes 1120. String of read color calls 1110 can be annotated with tint codes 1130. Each base of string of read color calls 1110 annotated with an inconsistent tint code ('a' or 'b') can be replaced in corrected string of read color calls 1140 with the missing color call '.'. Each base of string of read color calls 1110 annotated with a consistent tint code or not annotated at all can be copied to corrected string of read color calls 1140.

In various embodiments, the method shown in read color call correction 1100 in FIG. 11 can be used to correct a string of read color calls. The one or more inconsistent mismatches of the string of read color calls can be corrected by replacing each of the one or more inconsistent mismatches with the missing color call.

Embodiment for Correct to Singles

Figure 12:
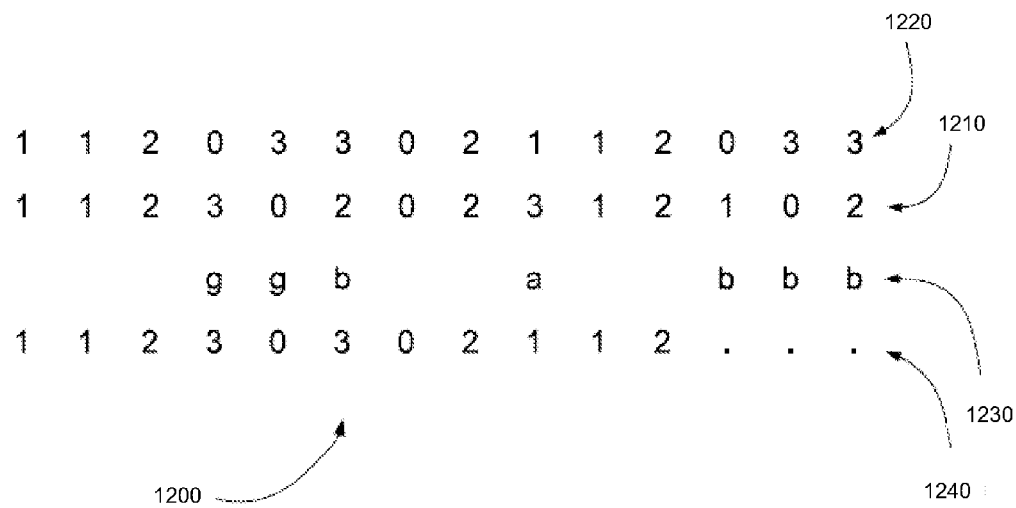
FIG. 12 is an exemplary read color call correction in which a read color call annotated as inconsistent and not adjacent to a read color call also annotated as inconsistent is corrected to the corresponding reference color call and all other read color calls annotated as inconsistent are corrected to the missing color call, in accordance with certain embodiments.

FIG. 12 is an exemplary read color call correction 1200 in which a read color call annotated as inconsistent and not adjacent to a read color call also annotated as inconsistent can be corrected to the corresponding reference color code and all other read color calls annotated as inconsistent are corrected to the missing color call, in accordance with certain embodiments. In read color call correction 1200, string of read color calls 1210 can be aligned with string of reference color codes 1220. String of read color calls 1210 can be annotated with tint codes 1230. Each base of string of read color calls 1210 annotated with an inconsistent tint code ('a' or 'b') and not adjacent to a read color call also annotated as inconsistent can be replaced with the corresponding color call of string of reference color codes 1220. All other read color calls annotated as inconsistent can be corrected to the missing color call '.'. Each base of string of read color calls 1210 annotated with a consistent tint code or not annotated at all can be copied to corrected string of read color calls 1240.

In various embodiments, the method shown in read color call correction 1200 in FIG. 12 can be used to correct a string of read color calls. The one or more inconsistent mismatches of the string of read color calls can be corrected by replacing each of the one or more inconsistent mismatches that is not adjacent to another inconsistent mismatch with its corresponding color call from the string of reference color codes. All other inconsistent mismatches can be replaced with the missing color call.

Embodiment to Correct to Consistent

In certain embodiments, correction can be performed to change the least number of positions so that no position in the corrected sequence, if reannotated, would be inconsistent. This correction method does not necessarily correct every inconsistent position. It can be both aggressive and conservative. It can be aggressive in that its correction is not necessarily to the reference, nor does it use the missing color. It can be conservative in that it makes as few corrections as possible. This method can makes use of the quality values for the color calls.

Ideally, most positions do not require correction. Therefore, the method can begin by making a copy of the read color calls. It can group the read color calls into blocks of inconsistent color calls that include two flanking neighbors. For each block, the position with the lowest quality value can be selected for correction, breaking ties at random with a uniform distribution. If the block contains exactly one missing color ('.'), the missing color can be corrected. If there is more than one missing color, correction may not possible, so the copy of the read color calls can be left unchanged.

Mathematically, if the color call $cc_k$ is selected for correction, it is set to the unique color that makes the entire block consistent. A block of read colors $d_1 d_2 d_3 \ldots d_n$ aligned to a reference $f_1 f_2 f_3 \ldots f_n$ is consistent with some number of base variants if $d_1 + d_2 + \ldots + d_n = f_1 + f_2 + \ldots + f_n$, where the addition operator is defined based on the multi-base code.

Table 7 shows how an addition operator can be defined for a dibase color code, in accordance with certain embodiments. Table 7 can be isomorphic to a Klein 4-Group, for example. Table 7 can be based on the dibase code shown in Table 5.

TABLE 7

| + | 0 | 1 | 2 | 3 |
|---|---|---|---|---|
| 0 | 0 | 1 | 2 | 3 |
| 1 | 1 | 0 | 3 | 2 |
| 2 | 2 | 3 | 0 | 1 |
| 3 | 3 | 2 | 1 | 0 |

If a block is not consistent, it can be made consistent by replacing any color call $d_i$ with another $d_i'$ such that $$d_1 + d_2 + \ldots + d_{i-1} + d_i' + d_{i+1} + \ldots + d_n = f_1 + f_2 + \ldots + f_n. \quad (1)$$

Solving for $d_i'$ by first adding $d_1 + d_2 + \ldots + d_n$ to both sides:

$$d_i + d_i' = f_1 + f_2 + \ldots + f_n + d_1 + d_2 + \ldots + d_n. \quad (2)$$

Nearly all $d_k$ on the left side disappear because, from Table 7, every color is its own inverse ($d_j + d_j = 0$), and 0 is the identity element ($x + 0 = 0 + x = x$). Then adding another $d_i$ to both sides yields an expression for $d_i'$.

$$d_i' = d_i + f_1 + f_2 + \ldots + f_n + d_1 + d_2 + \ldots + d_n \quad (3)$$

$$= d_i + \sum_{k=1}^{n} f_k + \sum_{k=1}^{n} d_k \quad (4)$$

The value $cc_i$ needed to correct position i is therefore expressed by the following compact Equation 5 in which the addition operation can be again defined by the addition Table 7.

$$cc_i = readcol_i + \sum_{k \in B} refcol_i + \sum_{k \in B} readcol_k \quad (5)$$

These methods and the equations pertain to blocks of any size.

Figure 13:
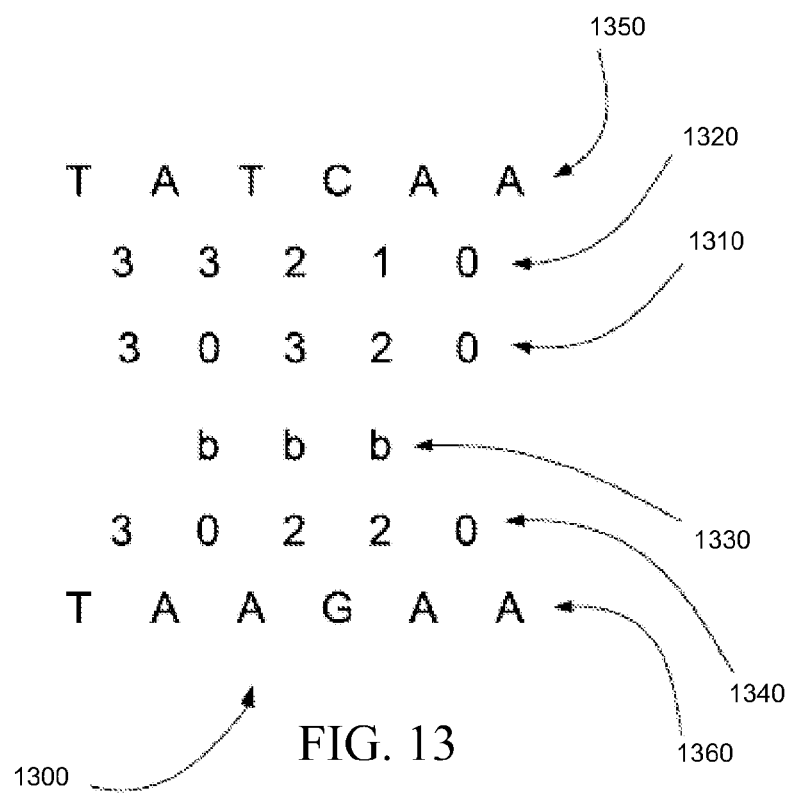
FIG. 13 is an exemplary read color call correction in which a block of color calls surrounding and including consecutive inconsistent mismatches is made consistent, in accordance with certain embodiments.

FIG. 13 is an exemplary read color call correction 1300 in which a block of color calls surrounding and including consecutive inconsistent mismatches can be made consistent, in accordance with certain embodiments. In read color call correction 1300, read block 1310 can be aligned with reference 1320. Read block 1310 can include three consecutive mismatches with reference 1320 in positions 2, 3, and 4. Read block 1310 can also include two non-mismatches in positions 1 and 5 that flank, or are adjacent to and on either side of the three consecutive mismatches. The three consecutive mismatches can be annotated with tint codes 1330 that show that the mismatches are inconsistent.

If position 3 is found to have the lowest quality value out of the five positions in read block 1310, position 3 can be corrected according to Equation 5. Substituting values from Table 7 into Equation 5, the replacement color call for position 3 can be 3+(3+3+2+1+0)+(3+0+3+2+0)=3+(3)+(2)=2, resulting in corrected read block 1340.

Corrected read block 1340 block can now look like two isolated color mismatches that, together with the correction, can be consistent with a two-base variant. If the read block starts with the base T, reference sequence 1350 and corrected read sequence 1360 can vary by two bases, for example.

In read color call correction 1300 shown in FIG. 13, the low-quality color call can be in the middle of its block, but in general it could be anywhere in the block, even one of the two flanking matches. For example, if the lowest quality color call is in position 5, the corrected read block can be consistent with a three-base variant.

In various embodiments, the method shown in read color call correction 1300 in FIG. 13 can be used to correct a string of read color calls. The one or more inconsistent mismatches of the string of read color calls can be corrected by performing a number of steps.

The one or more mismatches can be grouped into one or more blocks of mismatches. Each block of the one or more blocks of mismatches includes one or more adjacent mismatches and two non-mismatches adjacent to and on either side of the one or more adjacent mismatches. A color call for correction can be selected in each block that has a lowest quality value. An addition operator can be defined based on the multi-base code. In certain embodiments, the addition operator can be defined by Table 7. The color call for correction can be added with a sum of base color calls from a portion of the string of reference color codes corresponding to each block and a sum of read color calls in each block using the addition operator to produce a replacement color call. The color call for correction can be replaced with the replacement color in each block.

Decode Corrected Read Color Calls

Table 8 showing the outputs of a function that can decode a base color pair to a base for all possible inputs, in accordance with certain embodiments. According to the function depicted in Table 8, a base from a set of bases A, C, G, T, and X can be paired with a color call from a set of color calls 0, 1, 2, 3, and '.' to produce a base from the set of bases A, C, G, T, and X, where '.' represents a missing color call and X represents a missing base. The function can be based on the dibase code shown in Table 5.

TABLE 8

|   | 0 | 1 | 2 | 3 | . |
|---|---|---|---|---|---|
| A | A | C | G | T | X |
| C | C | A | T | G | X |
| G | G | T | A | C | X |
| T | T | G | C | A | X |
| X | X | X | X | X | X |

In certain embodiments, the function depicted in Table 8 can be used in a method for decoding corrected read color calls to read bases. This method can begin by restoring the first base of the read sequence using the last base of the primer, or whatever base is used as its surrogate, for example. This first base of the read sequence can be paired with the first color call of the string of corrected read calls producing the first base color pair. The first base color pair can be used to find the next base of the read sequence. The first base color pair can be input into the function depicted in Table 8 to produce the next base of the read sequence.

In order to decode the entire corrected read sequence, the function depicted in Table 8 can be applied iteratively by updating the base in the base color pair. For example, once the first base color pair and function depicted in Table 8 are used to decode the first color call into the next base, the next base can be paired with the next color call of the string of corrected read color calls producing a next base color pair. The next base color pair can be, in turn, used as input to the function depicted in Table 8 to decode the next color call into the updated next base. The function depicted in Table 8 can be applied iteratively until all the color call of the string of corrected read color calls have been decoded.

At-Least-Consistent Decoding

Figure 14:
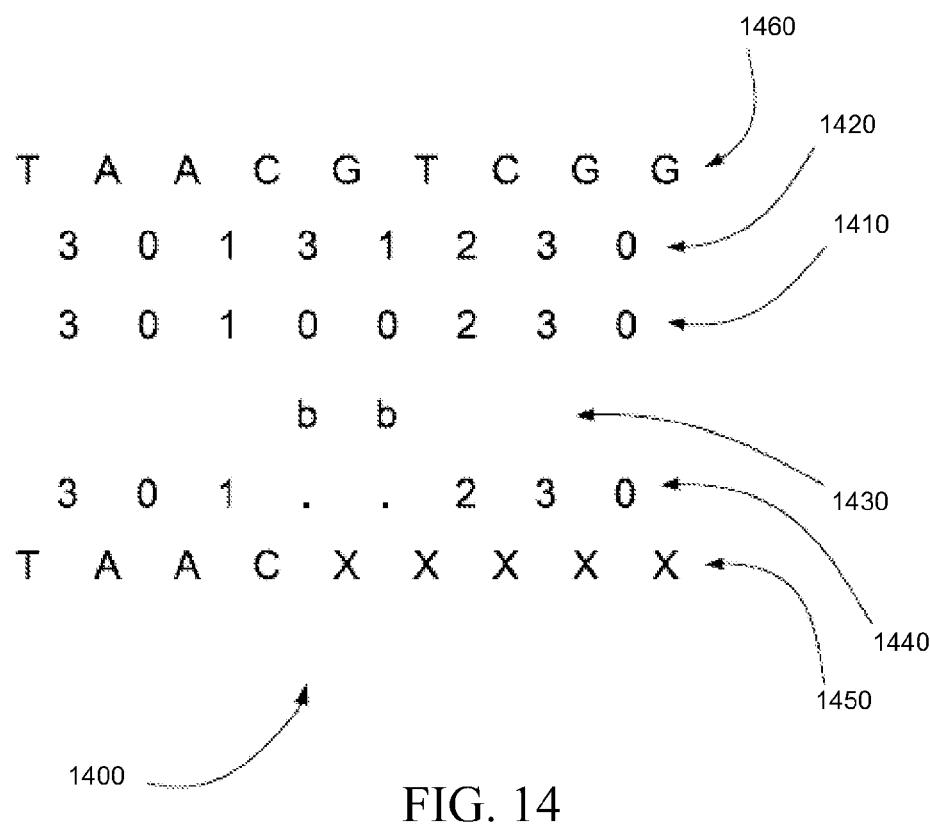
FIG. 14 is an exemplary read color call decoding showing how a missing base can be propagated to the end of the decoding, in accordance with certain embodiments.

FIG. 14 is an exemplary read color call decoding 1400 showing how a missing base can be propagated to the end of the decoding, in accordance with certain embodiments. In read color call decoding 1400, string of read color calls 1410 can be aligned with reference 1420. String of read color calls 1410 can include two consecutive mismatches with reference 1420 in positions 4 and 5. The two consecutive mismatches can be annotated with tint codes 1430 that show that the mismatches are inconsistent.

Under "Correct to missing", two consecutive mismatches in string of read color calls 1410 can be corrected by replacing the mismatches with the missing color call '.', producing string of corrected read color calls 1440. String of corrected read color calls 1440 can be then decoded using the decoding function depicted in Table 8, producing read sequence 1450 of FIG. 14. Read sequence 1450 shows that applying the decoding function depicted in Table 8 can propagate a missing base 'X' through to the end of a decoded sequence. Read sequence 1450 of FIG. 14 can differ more from reference sequence 1460 than the mismatches suggest.

To deal with this problem, the propagating string of missing bases must be broken. To this end, consider a maximal block of missing colors, that is, a subsequence of adjacent missing colors that is not part of a larger subsequence of adjacent missing colors. It is probably unreasonable to assume that every one of those missing colors should be equal to the reference, or that it is a read-error. It is probably reasonable, on the other hand, to assume that the block of missing colors is at least consistent with the reference (in this case, consistent with a zero- or one-base variant). A block can be consistent if the sum of its colors, using an addition operator as shown in Table 7, is equal to the corresponding sum in the reference. That is to say, the missing colors can transform the base before into the same base as the corresponding reference colors. Therefore, the read base can be set to the reference base immediately upon the end of a block of missing colors.

Figure 15:
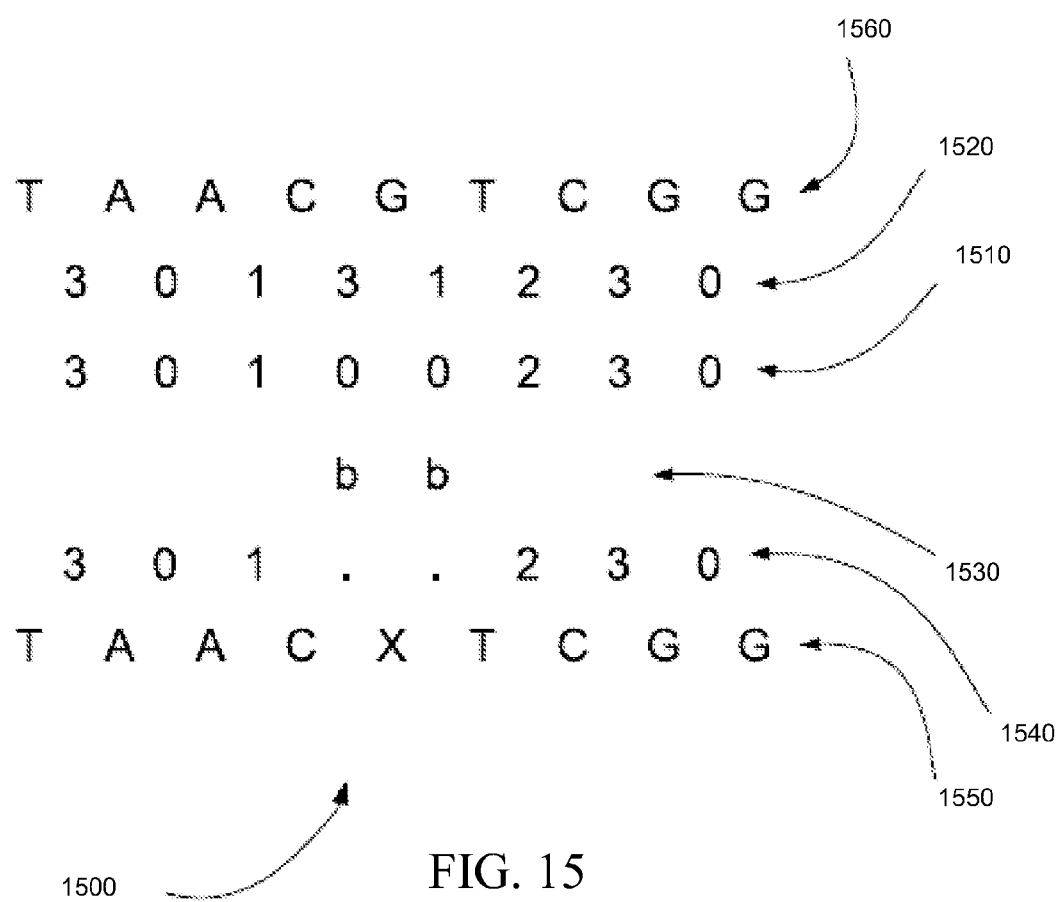
FIG. 15 is an exemplary read color call decoding showing how a read base can be set to the reference base immediately upon the end of a block of missing colors, in accordance with certain embodiments.

FIG. 15 is an exemplary read color call decoding 1500 showing how a read base can be set to the reference base immediately upon the end of a block of missing colors, in accordance with certain embodiments. As in FIG. 14, string of read color calls 1410 can be annotated with tint codes 1430, aligned with reference 1420, corrected to produce string of corrected read color calls 1440, and decoded using the decoding function depicted in Table 8.

However, if the end of a block of missing colors is found in string of corrected read color calls 1440 on FIG. 14, the decoding function depicted in Table 8 may not be used to decode the missing color call. Instead, the corresponding base from reference sequence 1460 of FIG. 15 can be used as the base for the read sequence. Decoding the end of a block of missing colors as the corresponding base from reference sequence 1460 breaks the propagation of missing bases and produces read sequence 1550. Note that base 'T' in position 6 of read sequence 1550 can be copied from reference sequence 1460. The end of the block of missing colors can be found in string of corrected read color calls 1440 by identifying a missing color call followed by a color call that is not a missing color call, for example.

Resequencing Method

Figure 16:
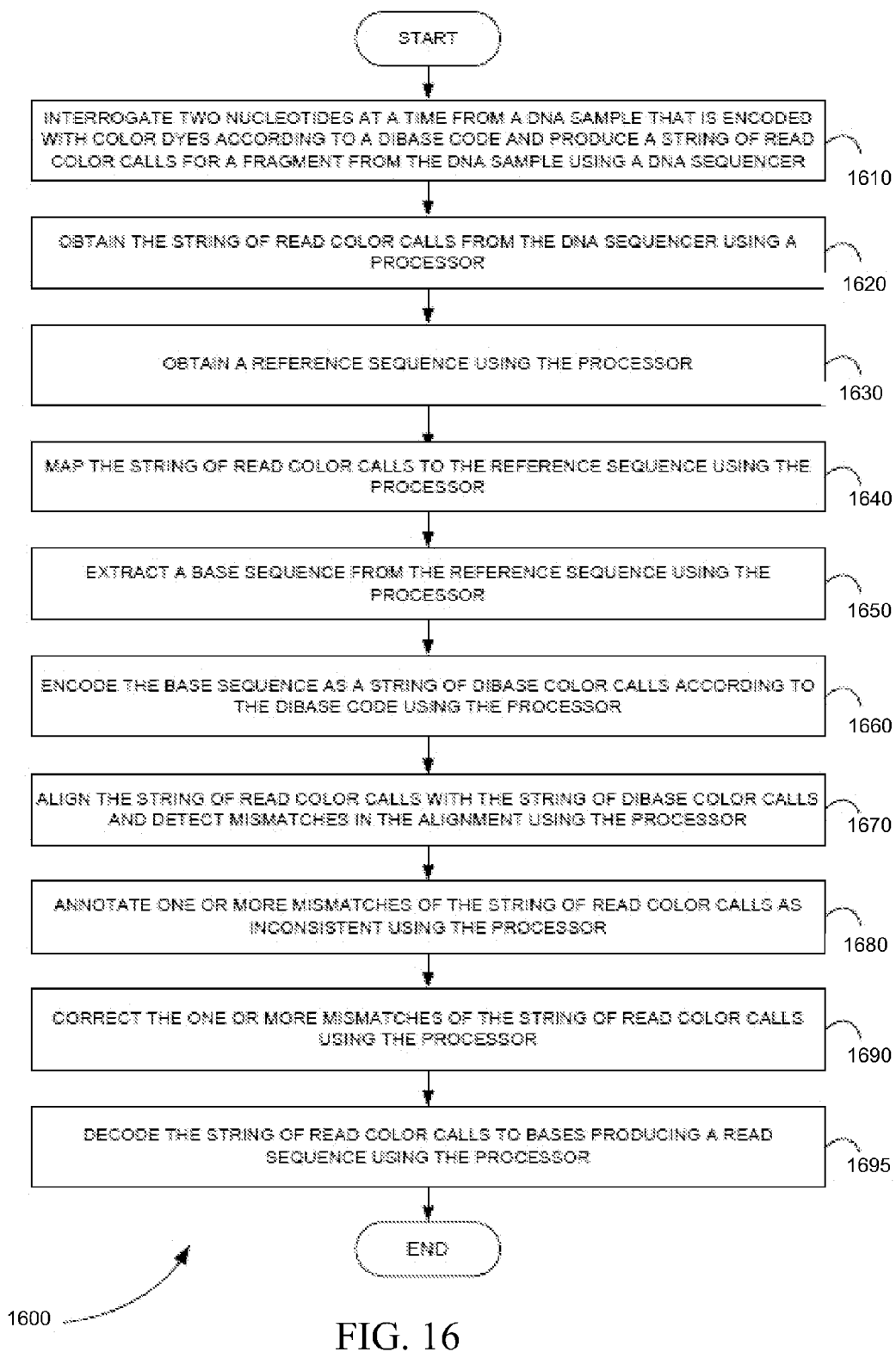
FIG. 16 is a flowchart showing a method for resequencing using color calls, in accordance with certain embodiments.

FIG. 16 is a flowchart showing a method 1600 for resequencing using color calls, in accordance with certain embodiments.

At 1610, two nucleotides can be interrogated at a time from a DNA sample that is encoded with color dyes according to a multi-base code and a string of read color calls are produced for a fragment from the DNA sample using a DNA sequencer.

At 1620, the string of read color calls can be obtained from the DNA sequencer using a processor.

At 1630, a reference sequence can be obtained using the processor. The reference sequence is obtained from a database, for example.

At 1640, the string of read color calls can be mapped to the reference sequence using the processor. In various embodiments, the reference sequence can be encoded as a string of multi-base color codes and the read color calls can be mapped to the encoded reference sequence. In other embodiments, the string of read color calls can be converted to a string of bases, and the string of bases can be mapped to the reference sequence. Mapping can involve identifying a substring of the reference sequence that has substantial similarity to the string of read color calls or string of bases. Various algorithms are known to those of skill in the art for mapping the string of read color calls or string of bases to the reference sequence.

In step 1650, a base sequence can be extracted from the reference sequence using the processor. In various embodiments, a substring of the reference sequence can be copied to the base sequence. Further, various haplotypes of the substring can be identified and an optimal haplotype can be selected for the base sequence.

In step 1660, the base sequence can be encoded as a string of reference color codes according to the multi-base code using the processor.

At 1670, the string of read color calls can be aligned with the string of reference color codes and mismatches in the alignment are detected using the processor.

At 1680, one or more mismatches of the string of read color calls can be annotated as inconsistent using the processor.

At 1690, the one or more mismatches of the string of read color calls can be corrected using the processor.

At 1695, the string of read color calls can be decoded to bases producing a read sequence using the processor.

Figure 19:
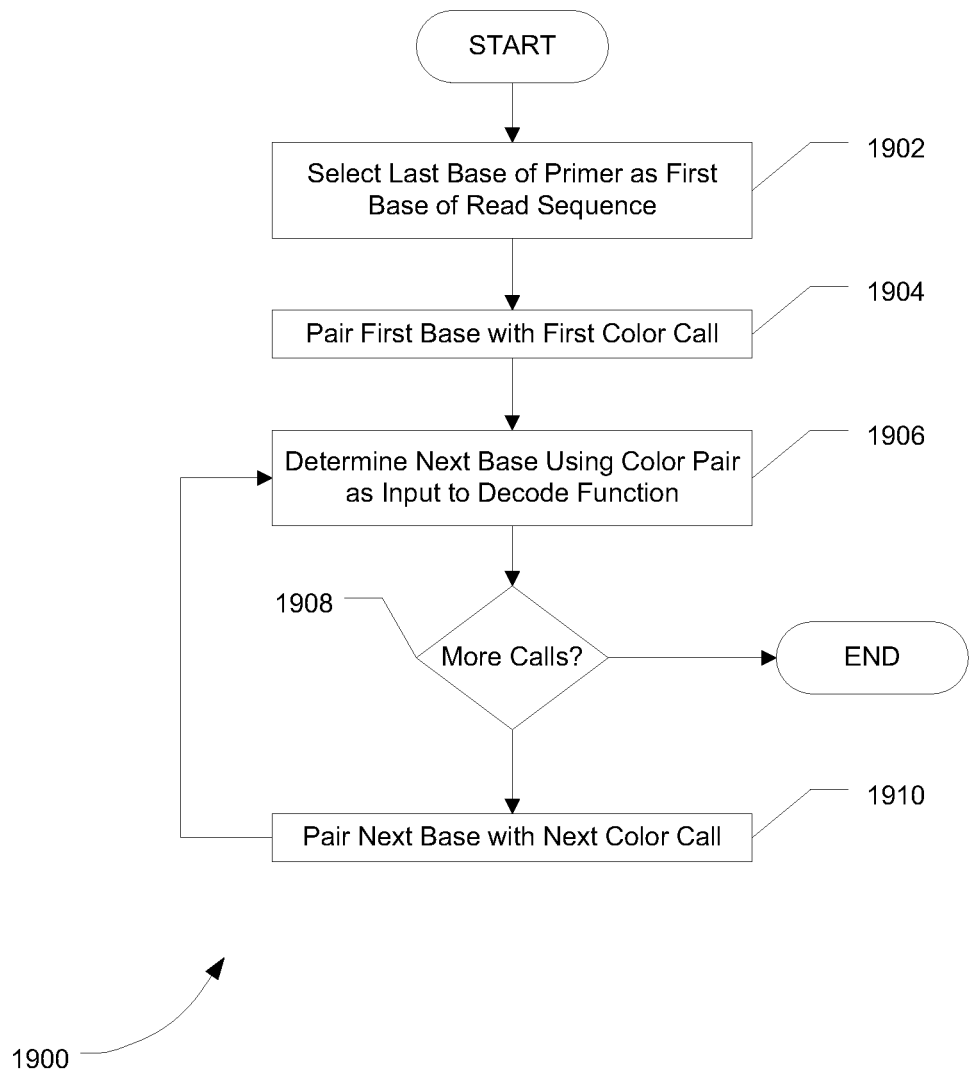
FIG. 19 is flowchart showing a method for decoding a string of read color calls, in accordance with certain embodiments.

FIG. 19 is a flowchart showing a method 1900 for decoding a string of read color calls to bases producing a read sequence using the function depicted in Table 8.

At 1902, the last base of the primer of the string of read color calls can be selected as the first base of the read sequence.

At 1904, the first base of the primer of the string of read color calls can be paired with a first color call of the string of read color calls to produce a base color pair.

At 1906, a next base of the read sequence can be determined by using the base color pair as an input base color pair to a decode function that decodes the input base color pair to an output base defined by the multi-base code. The decode function is depicted in Table 8, for example.

At 1908, it can be determined if there are additional color calls. If there are additional color calls, the next base can be paired with a next color call of the string of read color calls to produce the base color pair, as indicated at 1910. Alternatively, if there are no additional color calls, the method can end.

Figure 20:
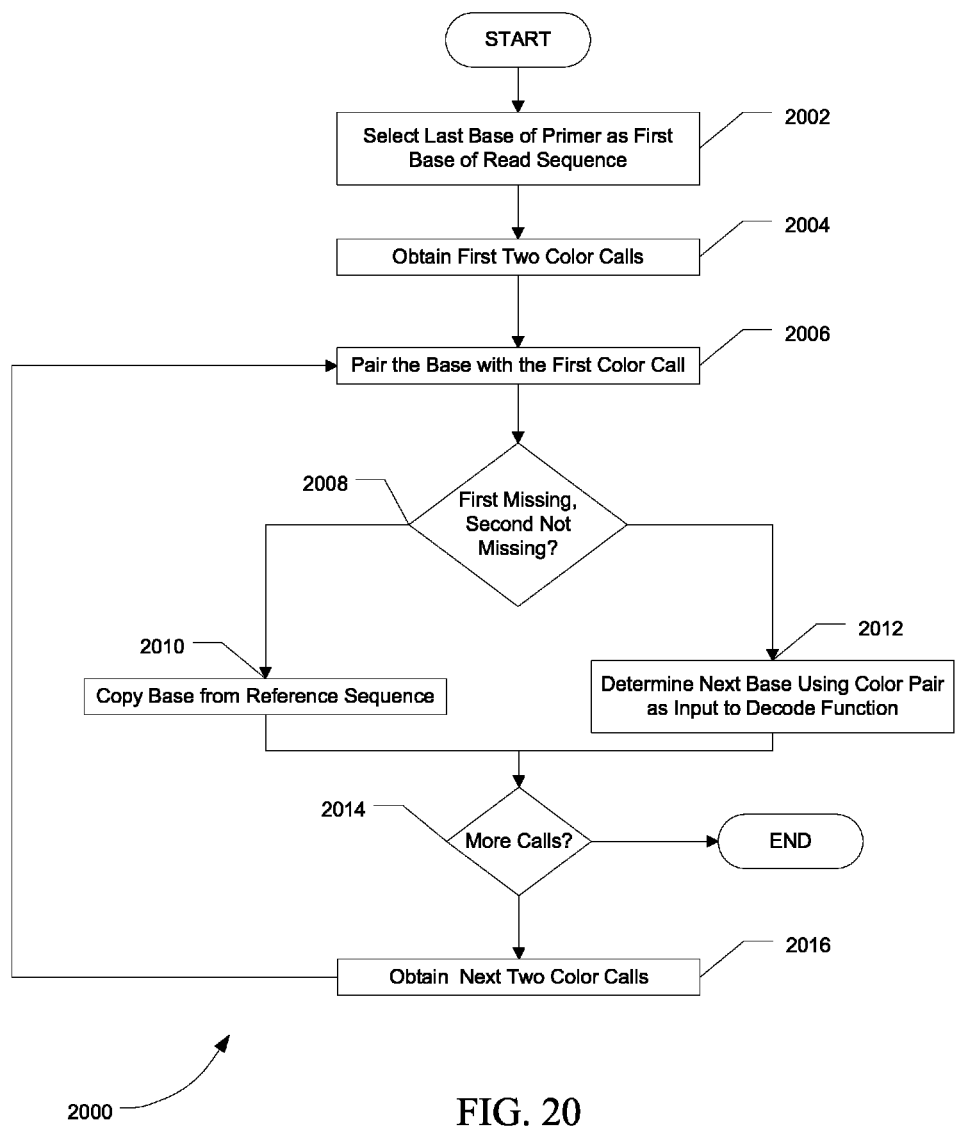
FIG. 20 is a flowchart showing another method for decoding a string of read color calls, in accordance with certain embodiments

FIG. 20 is a flowchart showing a method 2000 for decoding a string of read color calls to bases producing a read sequence using the function depicted in Table 8 or using a corresponding base from the reference sequence if the end of a block of missing colors is found in the string of corrected read color calls.

At 2002, the last base of the primer of the string of read color calls can be selected as the first base of the read sequence.

At 2004, the first two color calls can be obtained from the string of read color calls.

At 2006, the first base of the primer of the string of read color calls can be paired with the first color call of the first two color calls to produce a base color pair.

At 2008, it can be determined if the first color call of the first two color calls is a missing color call and the second call of the first two color calls is not a missing color call.

At 2010, when the first color call of the first two color calls is a missing color call and the second color call of the first two color calls is not a missing color call, a corresponding base can be copied from the reference sequence as the next base of the read sequence.

Alternatively, at 2012, the next base of the read sequence can be determined by using the base color pair as an input base color pair to a decode function that decodes the input base color pair to an output base defined by the multi-base code. The decode function is depicted in Table 8, for example.

At 2014, it can be determined if there are additional color calls. When there are no additional color calls, the method can end. Alternatively, when there are additional color calls, the next two color calls from the string of read color calls can be obtained, and at 2006, the next base of the read sequence can be paired with the first color call of the next two color calls of the string of read color calls to produce the base color pair.

Figure 21:
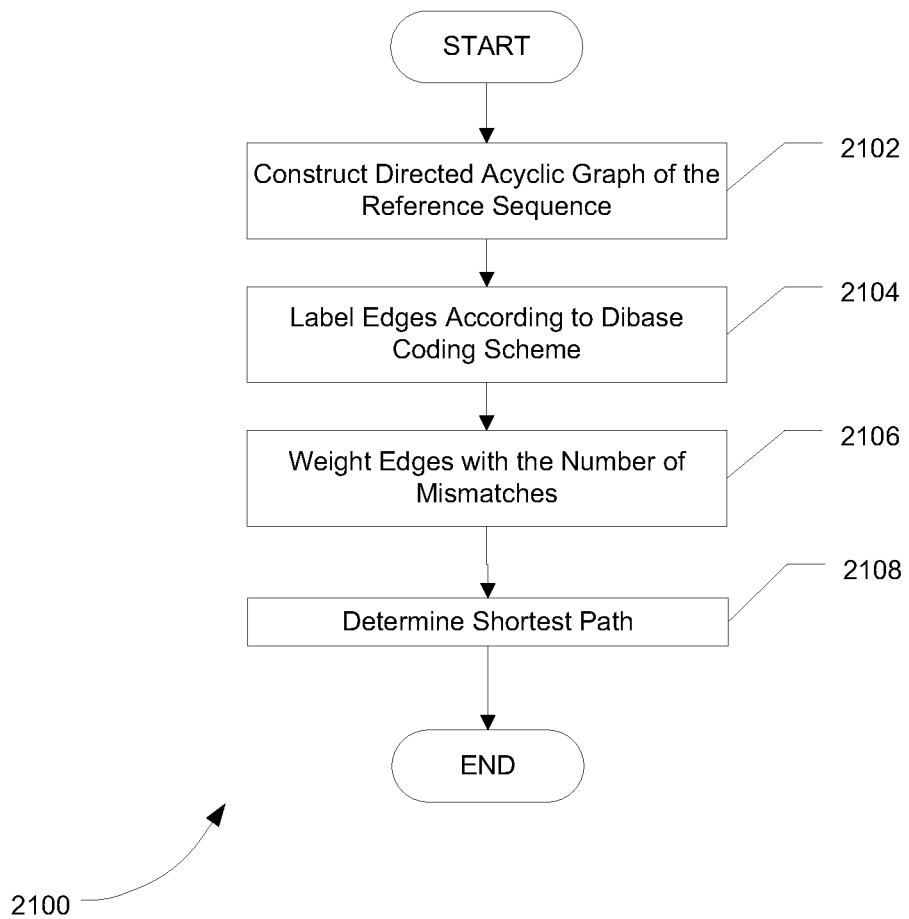
FIG. 21 is a flowchart showing a method of extracting an optimal haplotype, in accordance with certain embodiments.

FIG. 21 is a flowchart showing a method 2100 of extracting an optimal haplotype when the reference sequence includes one or more ambiguity codes.

At 2102, a directed acylic graph (DAG) can be constructed from the reference sequence. A vertex of the DAG can be created for each base in the IUB code, as indicated in Table 6, at each position in the reference sequence. For example, when the reference sequence includes a 'D', three vertices can be created for that position, one for 'A', one for 'G', and one for 'T'. Edges can be constructed to connect each vertex at one position in the reference sequence to each vertex at a next position in the reference sequence.

At 2104, the edges of the DAG can be labeled according to the color necessary to transform the vertex into the next vertex based on the multi-base coding scheme. For example, an edge going from an 'A' to a 'T' can be labeled with '3' according to the dibase coding scheme shown in Table 5.

At 2106, the edges of the DAG can be weighted based on the number of mismatches between the edge labels with the read color calls, either 0 or 1. For example, when the edge label matches the read color call at that position, the edge can be weighted 0, and when the edge label does not match the read color call at that position, the edge can be weighted 1.

At 2108, a shortest path can be found to traverse the DAG to identify an optimal haplotype. The shortest path can correspond to the haplotype having the lowest number of mismatches.

Resequencing Computer Program Product

In certain embodiments, a computer program product includes a non-trasitory computer-readable storage medium whose contents include a program with instructions being executed on a processor so as to perform a method for resequencing using color calls. This method can be performed by a system of distinct software modules.

Figure 17:
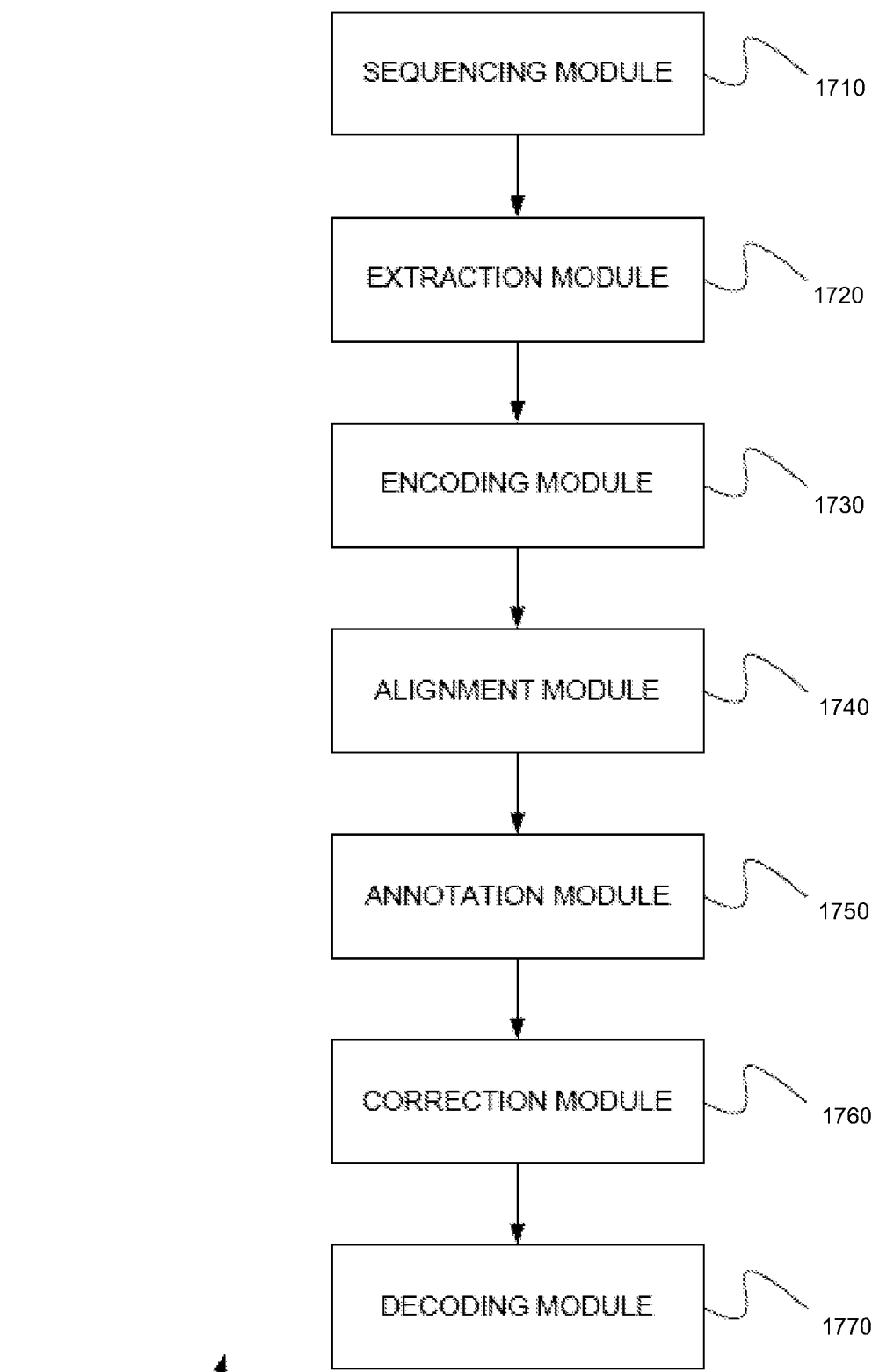
FIG. 17 is a schematic diagram of a system of distinct software modules that performs a method for resequencing using color calls, in accordance with certain embodiments.

FIG. 17 is a schematic diagram of a system 1700 of distinct software modules that performs a method for resequencing using color calls, in accordance with certain embodiments. System 1700 can include sequencing module 1710, extraction module 1720, encoding module 1730, alignment module 1740, annotation module 1750, correction module 1760, and decoding module 1770. These modules can perform a number of steps.

Sequencing module 1710 can obtain a string of read color calls from a DNA sequencer that interrogates two nucleotides at a time from a DNA sample that is encoded with color dyes according to a multi-base code and that produces the string of read color calls for a fragment from the DNA sample. Extraction module 1720 can obtain a reference sequence, can map the string of read color calls to the reference sequence, and can extract a base sequence from the reference sequence. The reference sequence can be obtained from a database, for example. Encoding module 1730 can encode the base sequence as a string of reference color codes according to the multi-base code. Alignment module 1740 can align the string of read color calls with the string of reference color codes and can detect mismatches in the alignment. Annotation module 1750 can annotate one or more mismatches of the string of read color calls as inconsistent using the annotation module. Correction module 1760 can correct the one or more mismatches of the string of read color calls. Decoding module 1770 can decode the string of read color calls to bases producing a read sequence.

Resequencing System

Figure 18:
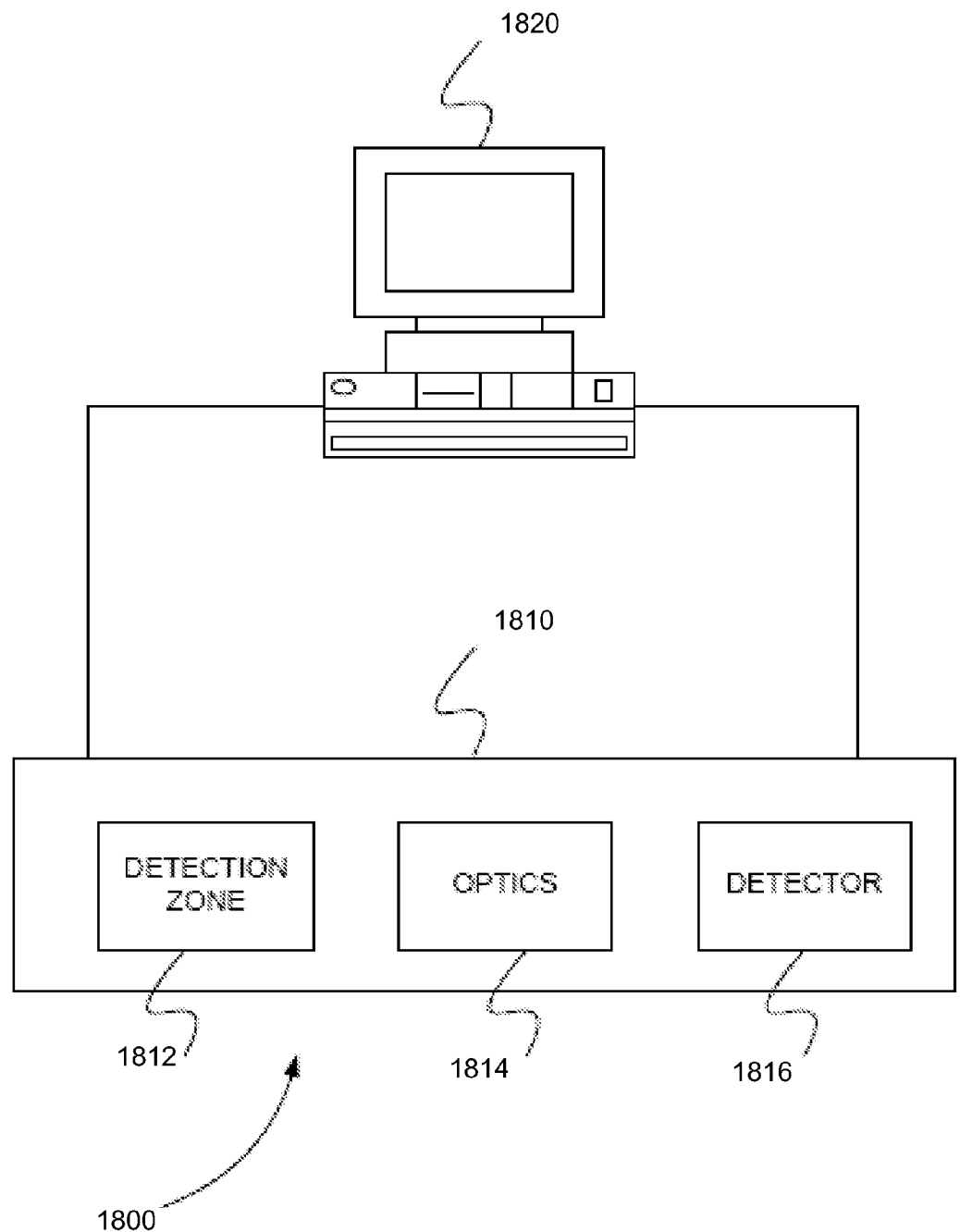
FIG. 18 is schematic diagram of a system for resequencing using color calls, in accordance with certain embodiments.

FIG. 18 is schematic diagram of a system 1800 for resequencing using color calls, in accordance with certain embodiments. System 1800 can include DNA sequencer 1810 and processor 1820. DNA sequencer 1810 can include, but is not limited to including, detection zone 1812, optics 1814, and detector 1816. DNA sequencer 1810 can be, but is not limited to, a next generation DNA sequencing (NGS) system such as the SOLiD™ platform. Processor 1820 can be, but is not limited to, a computer, microprocessor, or any device capable of sending and receiving control signals and data from DNA sequencer 1810 and processing data.

DNA sequencer 1810 can analyze a DNA sample. DNA sequencer 1810 can interrogate two nucleotides at a time from the DNA sample. The DNA sample can be encoded with color dyes according to a multi-base code. The multi-base code is, for example, the dibase code shown in Table 5. The DNA sample can be encoded with the color dyes by ligating a probe to a sequencing primer using ligase, for example. DNA sequencer 1810 can produce a string of read color calls for a fragment from the DNA sample. Processor 1820 can be in communication with the DNA sequencer 1810.

Processor 1820 can obtain the string of read color calls from the DNA sequencer. Processor 1820 can obtain a reference sequence. The reference sequence can be obtained from a database, for example. Processor 1820 can map the string of read color calls to the reference sequence. Processor 1820 can extract a base sequence from the reference sequence. Processor 1820 can encode the base sequence as a string of reference color codes according to the multi-base code. Processor 1820 can align the string of read color calls with the string of reference color codes and can detect mismatches in the alignment. Processor 1820 can annotate the mismatches of the string of read color calls as consistent or inconsistent. Processor 1820 can correct the string of read color calls. Finally, processor 1820 can decode the string of read color calls to bases producing a read sequence.

In a first aspect, a system for resequencing using color calls can include a processor. The processor can be configured to obtain a string of read color calls from the DNA sequencer. The string of read color calls encoded with a multi-base code. The processor can be further configured to obtain a reference sequence, map the string of read color calls to the reference sequence, extract a base sequence from the reference sequence, and encode the base sequence as a string of reference color codes according to the multi-base code. Further, the processor can be configured to align the string of read color calls with the string of reference color codes string of reference color codes and detects mismatches in the alignment, annotate one or more mismatches of the string of read color calls as inconsistent, correct the one or more mismatches of the string of read color calls, and decode the string of read color calls to bases producing a read sequence.

In embodiments of the first aspect, the system can further include the DNA sequencer in communication with the processor. The DNA sequencer can be configured to interrogate two nucleotides at a time from a DNA sample that is encoded with color dyes according to a multi-base code and produce the string of read color calls for a fragment from the DNA sample.

In embodiments of the first aspect, the processor can be configured to extract the base sequence from the reference sequence by replacing the ambiguity code with a missing base code and can encode the base sequence as a string of reference color codes by replacing the missing base code combined with any other base code with a missing color code, when mapping of the string of read color calls to the reference sequence includes an ambiguity code.

In embodiments of the first aspect, the processor can be configured to extract a base sequence from the reference sequence and encodes the base sequence as a string of reference color codes by extracting two or more base sequences from the reference sequence by replacing the one or more ambiguity codes with different possible bases, encoding each of the two or more base sequences according to the multi-base code producing two or more strings of base color calls, comparing each of the two or more strings of base color calls to the string of read color calls, and selecting a string of reference color codes that has a minimum number of mismatches with the string of read color calls as the string of reference color codes of the base sequence, when mapping of the string of read color calls to the reference sequence includes an ambiguity code.

In embodiments of the first aspect, the processor can be configured to correct the one or more mismatches of the string of read color calls by replacing each of the one or more mismatches with its corresponding color call from the string of reference color codes.

In embodiments of the first aspect, the processor can be configured to correct the one or more mismatches of the string of read color calls by replacing each of the one or more mismatches with a missing color call.

In embodiments of the first aspect, the processor can be configured to correct the one or more mismatches of the string of read color calls by replacing each mismatch of the one or more mismatches with its corresponding color call from the string of reference color codes if the each mismatch is not adjacent to another mismatch and with the missing color call if the each mismatch is adjacent to another mismatch.

In embodiments of the first aspect, the processor can be configured to correct the one or more mismatches of the string of read color calls by grouping the one or more mismatches into one or more blocks of mismatches, wherein each block of the one or more blocks of mismatches includes one or more adjacent mismatches and two non-mismatches adjacent to and on either side of the one or more adjacent mismatches, selecting a color call for correction in the each block that has a lowest quality value, defining an addition operator based on the multi-base code, adding the color call for correction with a sum of base color calls from a portion of the string of reference color codes corresponding to the each block and a sum of read color calls in the each block using the addition operator to produce a replacement color call, and replacing the color call for correction with the replacement color in the each block. In particular embodiments, the addition operator can define the sum of color call 0 and color call 0 as 0, color call 0 and color call 1 as 1, color call 0 and color call 2 as 2, color call 0 and color call 3 as 3, color call 1 and color call 0 as 1, color call 1 and color call 1 as 0, color call 1 and color call 2 as 3, color call 1 and color call 3 as 2, color call 2 and color call 0 as 2, color call 2 and color call 1 as 3, color call 2 and color call 2 as 0, color call 2 and color call 3 as 1, color call 3 and color call 0 as 3, color call 3 and color call 1 as 2, color call 3 and color call 2 as 1, and color call 3 and color call 3 as 0.

In embodiments of the first aspect, the processor can be configured to decode the string of read color calls to bases producing a read sequence by (a) selecting a last base of the primer of the string of read color calls as the first base of the read sequence, (b) pairing the first base of the primer of the string of read color calls with a first color call of the string of read color calls to produce a base color pair, (c) determining a next base of the read sequence by using the base color pair as an input base color pair to a decode function that decodes the input base color pair to an output base defined by the multi-base code, (d) pairing the next base with a next color call of the string of read color calls to produce the base color pair, and (e) performing steps (c)-(e) until all color calls of the string of read color calls have been used to determine the next base. In particular embodiments, the decode function can decode A0 to A, A1 to C, A2 to G, A3 to T, A. to X, C0 to C, C1 to A, C2 to T, C3 to G, C. to X, G0 to G, G1 to T, G2 to A, G3 to C, G. to X, T0 to T, T1 to G, T2 to C, T3 to A, T. to X, X0 to X, X1 to X, X2 to X, X3 to X, and X. to X.

In embodiments of the first aspect, the processor can be configured to decode the string of read color calls to bases producing a read sequence by (a) selecting a last base of the primer of the string of read color calls as the first base of the read sequence, (b) obtaining a first two color calls from the string of read color calls, (c) pairing the first base of the primer of the string of read color calls with a first color call of the first two color calls to produce a base color pair, (d) if the first color call of the first two color calls is a missing color call and a second color call of the first two color calls is not a missing color call, copying a corresponding reference base from the base sequence as a next base of the read sequence, otherwise determining the next base of the read sequence by using the base color pair as an input base color pair to a decode function that decodes the input base color pair to an output base defined by the multi-base code, (e) obtaining a next two color calls from the string of read color calls, (f) pairing the next base of the read sequence with a first color call of the next two color calls of the string of read color calls to produce the base color pair, (g) if the first color call of the next two color calls is a missing color call and a second color call of the next two color calls is not a missing color call, copying a corresponding reference base from the base sequence as the next base of the read sequence, otherwise determining the next base of the read sequence by using the base color pair as the input base color pair to the decode function that decodes, and (h) performing steps (e)-(h) until all color calls of the string of read color calls have been used to determine the next base. In particular embodiments, the decode function can decode A0 to A, A1 to C, A2 to G, A3 to T, A. to X, C0 to C, C1 to A, C2 to T, C3 to G, C. to X, G0 to G, G1 to T, G2 to A, G3 to C, G. to X, T0 to T, T1 to G, T2 to C, T3 to A, T. to X, X0 to X, X1 to X, X2 to X, X3 to X, and X. to X.

In a second aspect, a method for resequencing using color calls can include obtaining the string of read color calls from the DNA sequencer using a processor. The method can further include obtaining a reference sequence using the processor; mapping the string of read color calls to the reference sequence using the processor; extracting a base sequence from the reference sequence using the processor; and encoding the base sequence as a string of reference color codes according to the multi-base code using the processor. Further, the method can include aligning the string of read color calls with the string of reference color codes and detecting mismatches in the alignment using the processor; annotating one or more mismatches of the string of read color calls as inconsistent using the processor; correcting the one or more mismatches of the string of read color calls using the processor; and decoding the string of read color calls to bases producing a read sequence using the processor.

In embodiments of the second aspect, the method can further include interrogating two nucleotides at a time from a DNA sample that is encoded with color dyes according to the multi-base code and producing the string of read color calls for a fragment from the DNA sample using a DNA sequencer.

In embodiments of the second aspect, the method can include extracting the base sequence from the reference sequence by replacing the ambiguity code with a missing base code and encoding the base sequence a string of reference color codes by replacing the missing base code combined with any other base code with a missing color code, when the mapping of the string of read color calls to the reference sequence includes an ambiguity code.

In embodiments of the second aspect, the method can include extracting a base sequence from the reference sequence and encodeing the base sequence as a string of reference color codes by extracting two or more base sequences from the reference sequence by replacing the one or more ambiguity codes with different possible bases, encoding each of the two or more base sequences according to the multi-base code producing two or more strings of base color calls, comparing each of the two or more strings of base color calls to the string of read color calls, and selecting a string of reference color codes that has a minimum number of mismatches with the string of read color calls as the string of reference color codes of the base sequence, when the mapping of the string of read color calls to the reference sequence includes one or more ambiguity codes.

In embodiments of the second aspect, the method can include correcting the one or more mismatches of the string of read color calls by replacing each of the one or more mismatches with its corresponding color call from the string of reference color codes.

In embodiments of the second aspect, the method can include correcting the one or more mismatches of the string of read color calls by replacing each of the one or more mismatches with a missing color call.

In embodiments of the second aspect, the method can include correcting the one or more mismatches of the string of read color calls by replacing each mismatch of the one or more mismatches with its corresponding color call from the string of reference color codes if the each mismatch is not adjacent to another mismatch and with the missing color call if the each mismatch is adjacent to another mismatch.

In embodiments of the second aspect, the method can include correcting the one or more mismatches of the string of read color calls by grouping the one or more mismatches into one or more blocks of mismatches, wherein each block of the one or more blocks of mismatches includes one or more adjacent mismatches and two non-mismatches adjacent to and on either side of the one or more adjacent mismatches, selecting a color call for correction in the each block that has a lowest quality value, defining an addition operator based on the multi-base code, adding the color call for correction with a sum of base color calls from a portion of the string of reference color codes corresponding to the each block and a sum of read color calls in the each block using the addition operator to produce a replacement color call, and replacing the color call for correction with the replacement color in the each block. In particular embodiments, the addition operator can define the sum of color call 0 and color call 0 as 0, color call 0 and color call 1 as 1, color call 0 and color call 2 as 2, color call 0 and color call 3 as 3, color call 1 and color call 0 as 1, color call 1 and color call 1 as 0, color call 1 and color call 2 as 3, color call 1 and color call 3 as 2, color call 2 and color call 0 as 2, color call 2 and color call 1 as 3, color call 2 and color call 2 as 0, color call 2 and color call 3 as 1, color call 3 and color call 0 as 3, color call 3 and color call 1 as 2, color call 3 and color call 2 as 1, and color call 3 and color call 3 as 0.

In embodiments of the second aspect, the method can include decoding the string of read color calls to bases producing a read sequence by (a) selecting a last base of the primer of the string of read color calls as the first base of the read sequence, (b) pairing the first base of the primer of the string of read color calls with a first color call of the string of read color calls to produce a base color pair, (c) determining a next base of the read sequence by using the base color pair as an input base color pair to a decode function that decodes the input base color pair to an output base defined by the multi-base code, (d) pairing the next base with a next color call of the string of read color calls to produce the base color pair, and (e) performing steps (c)-(e) until all color calls of the string of read color calls have been used to determine the next base. In particular embodiments, the decode function can decode A0 to A, A1 to C, A2 to G, A3 to T, A. to X, C0 to C, C1 to A, C2 to T, C3 to G, C. to X, G0 to G, G1 to T, G2 to A, G3 to C, G. to X, T0 to T, T1 to G, T2 to C, T3 to A, T. to X, X0 to X, X1 to X, X2 to X, X3 to X, and X. to X.

In embodiments of the second aspect, the method can include decoding the string of read color calls to bases producing a read sequence by (a) selecting a last base of the primer of the string of read color calls as the first base of the read sequence, (b) obtaining a first two color calls from the string of read color calls, (c) pairing the first base of the primer of the string of read color calls with a first color call of the first two color calls to produce a base color pair, (d) if the first color call of the first two color calls is a missing color call and a second color call of the first two color calls is not a missing color call, copying a corresponding reference base from the base sequence as a next base of the read sequence, otherwise determining the next base of the read sequence by using the base color pair as an input base color pair to a decode function that decodes the input base color pair to an output base defined by the multi-base code, (e) obtaining a next two color calls from the string of read color calls, (f) pairing the next base of the read sequence with a first color call of the next two color calls of the string of read color calls to produce the base color pair, (g) if the first color call of the next two color calls is a missing color call and a second color call of the next two color calls is not a missing color call, copying a corresponding reference base from the base sequence as the next base of the read sequence, otherwise determining the next base of the read sequence by using the base color pair as the input base color pair to the decode function that decodes, and (h) performing steps (e)-(h) until all color calls of the string of read color calls have been used to determine the next base. In particular embodiments, the decode function can decode A0 to A, A1 to C, A2 to G, A3 to T, A. to X, C0 to C, C1 to A, C2 to T, C3 to G, C. to X, G0 to G, G1 to T, G2 to A, G3 to C, G. to X, T0 to T, T1 to G, T2 to C, T3 to A, T. to X, X0 to X, X1 to X, X2 to X, X3 to X, and X. to X.

In a third aspect, a computer program product can comprise a non-transitory computer readable storage medium whose contents include a program with instructions being executed on a processor so as to perform a method for resequencing using color calls. The method can include providing a system, wherein the system comprises distinct software modules. The distinct software modules can comprise a sequencing module, an extraction module, an encoding module, an alignment module, an annotation module, a correction module, and a decoding module. The method can further include obtaining a string of read color calls from a DNA sequencer that interrogates two nucleotides at a time from a DNA sample that is encoded with color dyes according to a multi-base code and that produces the string of read color calls for a fragment from the DNA sample using the sequencing module; obtaining a reference sequence using the extraction module; mapping the string of read color calls to the reference sequence using the extraction module; extracting a base sequence from the reference sequence using the extraction module; encoding the base sequence as a string of reference color codes according to the multi-base code using the encoding module; aligning the string of read color calls with the string of reference color codes and detecting mismatches in the alignment using the alignment module; annotating one or more mismatches of the string of read color calls as inconsistent using the annotation module; correcting the one or more mismatches of the string of read color calls using the correction module; and decoding the string of read color calls to bases producing a read sequence using the decoding module.

While the principles of the present teachings have been described in connection with specific embodiments of control systems and sequencing platforms, it should be understood clearly that these descriptions are made only by way of example and are not intended to limit the scope of the present teachings or claims. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalents.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A system for resequencing a DNA fragment using color calls, comprising:
a DNA sequencer in communication with a processor;
the DNA sequencer configured to:
perform a sequence-by-ligation process using a DNA sample and probes labeled with color dyes, wherein the probes interrogate two or more nucleotides at a time with the color dyes according to a multi-base code, the sequence-by-ligation process comprising:
performing multiple ligation reaction cycles, wherein a ligated probe is generated with each ligation reaction cycle,
detecting the ligated probe after the ligation reaction cycle to obtain a color call for the ligated probe, and
producing a string of read color calls for a DNA fragment from the DNA sample, the string of read color calls encoded with the multi-base code; and
the processor configured to:
obtain the string of read color calls from the DNA sequencer,
obtain a reference sequence,
map the string of read color calls to the reference sequence,
extract a base sequence from the reference sequence,
encode the base sequence as a string of reference color codes according to the multi-base code,
align the string of read color calls with the string of reference color codes and detect mismatches in the alignment,
annotate one or more mismatches of the string of read color calls as inconsistent,
correct the one or more mismatches of the string of read color calls, wherein the processor corrects at least one mismatch of the string of read color calls by replacing the mismatch with its corresponding color call from the string of reference color codes, and
decode the string of read color calls to bases producing a read sequence for the DNA fragment.

2. The system of claim 1, wherein if the mapping of the string of read color calls to the reference sequence includes an ambiguity code, the processor extracts the base sequence from the reference sequence by replacing the ambiguity code with a missing base code and encodes the base sequence as a string of reference color codes by replacing the missing base code combined with any other base code with a missing color code.

3. The system of claim 1, wherein if the mapping of the string of read color calls to the reference sequence includes one or more ambiguity codes, the processor extracts a base sequence from the reference sequence and encodes the base sequence as a string of reference color codes by:
extracting two or more base sequences from the reference sequence by replacing the one or more ambiguity codes with different possible bases,
encoding each of the two or more base sequences according to the multi-base code producing two or more strings of base color calls,
comparing each of the two or more strings of base color calls to the string of read color calls, and
selecting a string of reference color codes that has a minimum number of mismatches with the string of read color calls as the string of reference color codes of the base sequence.

4. The system of claim 1, wherein the processor corrects the one or more mismatches of the string of read color calls by replacing each of the one or more mismatches with its corresponding color call from the string of reference color codes.

5. The system of claim 1, wherein the processor corrects at least one of the one or more mismatches of the string of read color calls by replacing the at least one mismatch with a missing color call.

6. The system of claim 1, wherein the processor corrects at least one of the one or more mismatches of the string of read color calls by replacing the at least one mismatch of the one or more mismatches with its corresponding color call from the string of reference color codes if the mismatch is not adjacent to another mismatch and with the missing color call if the mismatch is adjacent to another mismatch.

7. The system of claim 1, wherein the processor corrects the one or more mismatches of the string of read color calls by
grouping the one or more mismatches into one or more blocks of mismatches, wherein each block of the one or more blocks of mismatches includes one or more adjacent mismatches and two non-mismatches adjacent to and on either side of the one or more adjacent mismatches,
selecting a color call for correction in the each block that has a lowest quality value,
defining an addition operator based on the multi-base code,
adding the color call for correction with a sum of base color calls from a portion of the string of reference color codes corresponding to the each block and a sum of read color calls in the each block using the addition operator to produce a replacement color call, and
replacing the color call for correction with the replacement color in the each block.

8. The system of claim 7, wherein the addition operator defines the sum of color call 0 and color call 0 as 0, color call 0 and color call 1 as 1, color call 0 and color call 2 as 2, color call 0 and color call 3 as 3, color call 1 and color call 0 as 1, color call 1 and color call 1 as 0, color call 1 and color call 2 as 3, color call 1 and color call 3 as 2, color call 2 and color call 0 as 2, color call 2 and color call 1 as 3, color call 2 and color call 2 as 0, color call 2 and color call 3 as 1, color call 3 and color call 0 as 3, color call 3 and color call 1 as 2, color call 3 and color call 2 as 1, and color call 3 and color call 3 as 0.

9. The system of claim 1, wherein the processor decodes the string of read color calls to bases producing a read sequence by
(a) selecting a last base of the primer of the string of read color calls as the first base of the read sequence,
(b) pairing the first base of the primer of the string of read color calls with a first color call of the string of read color calls to produce a base color pair,
(c) determining a next base of the read sequence by using the base color pair as an input base color pair to a decode function that decodes the input base color pair to an output base defined by the multi-base code,
(d) pairing the next base with a next color call of the string of read color calls to produce the base color pair, and
(e) performing steps (c)-(e) until all color calls of the string of read color calls have been used to determine the next base.

10. The system of claim 9, wherein the decode function decodes A0 to A, A1 to C, A2 to G, A3 to T, A. to X, C0 to C, C1 to A, C2 to T, C3 to G, C. to X, G0 to G, G1 to T, G2 to A, G3 to C, G. to X, T0 to T, T1 to G, T2 to C, T3 to A, T. to X, X0 to X, X1 to X, X2 to X, X3 to X, and X. to X.

11. The system of claim 1, wherein the processor decodes the string of read color calls to bases producing a read sequence by
(a) selecting a last base of the primer of the string of read color calls as the first base of the read sequence,
(b) obtaining a first two color calls from the string of read color calls,
(c) pairing the first base of the primer of the string of read color calls with a first color call of the first two color calls to produce a base color pair,
(d) if the first color call of the first two color calls is a missing color call and a second color call of the first two color calls is not a missing color call, copying a corresponding reference base from the base sequence as a next base of the read sequence, otherwise determining the next base of the read sequence by using the base color pair as an input base color pair to a decode function that decodes the input base color pair to an output base defined by the multi-base code,
(e) obtaining a next two color calls from the string of read color calls,
(f) pairing the next base of the read sequence with a first color call of the next two color calls of the string of read color calls to produce the base color pair,
(g) if the first color call of the next two color calls is a missing color call and a second color call of the next two color calls is not a missing color call, copying a corresponding reference base from the base sequence as the next base of the read sequence, otherwise determining the next base of the read sequence by using the base color pair as the input base color pair to the decode function that decodes, and
(h) performing steps (e)-(h) until All color calls of the string of read color calls have been used to determine the next base.

12. The system of claim 11, wherein the decode function decodes A0 to A, A1 to C, A2 to G, A3 to T, A. to X, C0 to C, C1 to A, C2 to T, C3 to G, C. to X, G0 to G, G1 to T, G2 to A, G3 to C, G. to X, T0 to T, T1 to G, T2 to C, T3 to A, T. to X, X0 to X, X1 to X, X2 to X, X3 to X, and X. to X.

13. The system of claim 1, wherein the multi-base code is a dibase code.

14. A method for resequencing a DNA fragment using color calls, comprising:
performing a sequence-by-ligation process using a DNA sequencer, a DNA sample, and probes labeled with color dyes, wherein the probes interrogate two nucleotides at a time with the color dyes according to a multi-base code, the sequence-by-ligation process comprising:
performing multiple ligation reaction cycles, wherein a ligated probe is generated with each ligation reaction cycle,
detecting the ligated probe after the ligation reaction cycle to obtain a color call for the ligated probe,
producing a string of read color calls for a DNA fragment from the DNA sample, the string of read color calls encoded with the multi-base code,
obtaining the string of read color calls from the DNA sequencer using a processor;
obtaining a reference sequence using the processor;
mapping the string of read color calls to the reference sequence using the processor;
extracting a base sequence from the reference sequence using the processor;
encoding the base sequence as a string of reference color codes according to the multi-base code using the processor;
aligning the string of read color calls with the string of reference color codes and detecting mismatches in the alignment using the processor;
annotating one or more mismatches of the string of read color calls as inconsistent using the processor;

correcting the one or more mismatches of the string of read color calls using the processor, wherein the processor corrects at least one mismatch of the string of read color calls by replacing the mismatch with its corresponding color call from the string of reference color codes; and decoding the string of read color calls to bases producing a read sequence for the DNA fragment using the processor.

15. The method of claim 14, further comprising extracting the base sequence from the reference sequence by replacing the ambiguity code with a missing base code and encoding the base sequence a string of reference color codes by replacing the missing base code combined with any other base code with a missing color code, when the mapping of the string of read color calls to the reference sequence includes an ambiguity code.

16. The method of claim 14, further comprising correcting the one or more mismatches of the string of read color calls by replacing each of the one or more mismatches with its corresponding color call from the string of reference color codes.

17. The method of claim 14, further comprising correcting at least one of the one or more mismatches of the string of read color calls by replacing the at least one mismatch of the one or more mismatches with its corresponding color call from the string of reference color codes if the mismatch is not adjacent to another mismatch and with the missing color call if the mismatch is adjacent to another mismatch.

18. The method of claim 14, further comprising decoding the string of read color calls to bases producing a read sequence by
   (a) selecting a last base of the primer of the string of read color calls as the first base of the read sequence,
   (b) pairing the first base of the primer of the string of read color calls with a first color call of the string of read color calls to produce a base color pair,
   (c) determining a next base of the read sequence by using the base color pair as an input base color pair to a decode function that decodes the input base color pair to an output base defined by the multi-base code,
   (d) pairing the next base with a next color call of the string of read color calls to produce the base color pair, and
   (e) performing steps (c)-(e) until All color calls of the string of read color calls have been used to determine the next base.

* * * * *